US009527891B2

(12) United States Patent
Sirard

(10) Patent No.: US 9,527,891 B2
(45) Date of Patent: Dec. 27, 2016

(54) IMMUNOADJUVANT FLAGELLIN-BASED COMPOUNDS AND USE THEREOF

(75) Inventor: Jean-Claude Sirard, Lille (FR)

(73) Assignees: INSERM (Institut National de la Santé et de la Recherche Médicale), Paris (FR); INSTITUT PASTEUR DE LILLE, Lille (FR)

( * ) Notice: Subject to any disclaimer, the term of this patent is extended or adjusted under 35 U.S.C. 154(b) by 333 days.

(21) Appl. No.: 13/000,167

(22) PCT Filed: Jun. 23, 2009

(86) PCT No.: PCT/EP2009/057836
§ 371 (c)(1),
(2), (4) Date: Dec. 20, 2010

(87) PCT Pub. No.: WO2009/156405
PCT Pub. Date: Dec. 30, 2009

(65) Prior Publication Data

US 2011/0110962 A1 May 12, 2011

(30) Foreign Application Priority Data

Jun. 25, 2008 (EP) .................................... 08305327

(51) Int. Cl.
*C07K 14/255* (2006.01)
*A61K 39/39* (2006.01)
*A61K 39/00* (2006.01)

(52) U.S. Cl.
CPC ............. *C07K 14/255* (2013.01); *A61K 39/39* (2013.01); *A61K 2039/541* (2013.01); *A61K 2039/55516* (2013.01)

(58) Field of Classification Search
None
See application file for complete search history.

(56) References Cited

U.S. PATENT DOCUMENTS

2006/0257415 A1* 11/2006 Sirard et al. ............... 424/184.1

FOREIGN PATENT DOCUMENTS

| | | | |
|---|---|---|---|
| WO | WO 2004/022092 | * | 3/2004 |
| WO | WO2004/022092 | | 3/2004 |
| WO | WO2005/107381 | | 11/2005 |
| WO | WO2006078657 A2 | * | 7/2006 |
| WO | WO 2006/081007 A2 | * | 8/2006 |
| WO | WO2009/128950 | | 10/2009 |

OTHER PUBLICATIONS

Uniprot accession #P06179 Jan. 1, 1998.*
Honko et al., Flagellin is effective adjuvant for immunization against lethal respiratory challenge with Yersinia pestis, Infection and Immunity, 74(2); 1113-1120 (Feb. 2006).
Nempont et al., Deletion of flagellin's hypervariable region abrogates antibody-mediated neutralization and systemic activation of TLR5-dependent immunity, Journal of Immunology, 181(3); 2036-2043 (Aug. 2008).
Nempont, et al., Deletion of Flagellin's Hypervariable Region Abrogates Antibody-Mediated Neutralization and Systemic Activation of TLR5-Dependent Immunity, The Journal of Immunology, 2008, vol. 181, pp. 2036-2042.
Smith, et al., "Toll-like receptor 5 recognizes a conserved site on flagellin required for protofilament formation and bacterial motility." Nature Immunology; Dec. 2003; pp. 1247-1253; vol. 4, Issue 12.

* cited by examiner

*Primary Examiner* — Oluwatosin Ogunbiyi
(74) *Attorney, Agent, or Firm* — Whitham, Curtis & Cook, P.C.

(57) ABSTRACT

The present invention relates to novel peptide compounds derived from flagellin originating from *Salmonella enterica* that exhibit an in vivo immune adjuvant activity.

7 Claims, 14 Drawing Sheets

SEQUENCE LISTING

<160> NUMBER OF SEQ ID NOS: 35

<210> SEQ ID NO 1
<211> LENGTH: 494
<212> TYPE: PRT
<213> ORGANISM: Salmonella enterica

<400> SEQUENCE: 1

```
Ala Gln Val Ile Asn Thr Asn Ser Leu Ser Leu Leu Thr Gln Asn Asn
 1               5                  10                  15

Leu Asn Lys Ser Gln Ser Ala Leu Gly Thr Ala Ile Glu Arg Leu Ser
             20                  25                  30

Ser Gly Leu Arg Ile Asn Ser Ala Lys Asp Asp Ala Ala Gly Gln Ala
         35                  40                  45

Ile Ala Asn Arg Phe Thr Ala Asn Ile Lys Gly Leu Thr Gln Ala Ser
     50                  55                  60

Arg Asn Ala Asn Asp Gly Ile Ser Ile Ala Gln Thr Thr Glu Gly Ala
 65                  70                  75                  80

Leu Asn Glu Ile Asn Asn Asn Leu Gln Arg Val Arg Glu Leu Ala Val
                 85                  90                  95

Gln Ser Ala Asn Ser Thr Asn Ser Gln Ser Asp Leu Asp Ser Ile Gln
            100                 105                 110

Ala Glu Ile Thr Gln Arg Leu Asn Glu Ile Asp Arg Val Ser Gly Gln
        115                 120                 125

Thr Gln Phe Asn Gly Val Lys Val Leu Ala Gln Asp Asn Thr Leu Thr
    130                 135                 140

Ile Gln Val Gly Ala Asn Asp Gly Glu Thr Ile Asp Ile Asp Leu Lys
145                 150                 155                 160

Gln Ile Asn Ser Gln Thr Leu Gly Leu Asp Thr Leu Asn Val Gln Gln
                165                 170                 175

Lys Tyr Lys Val Ser Asp Thr Ala Ala Thr Val Thr Gly Tyr Ala Asp
            180                 185                 190

Thr Thr Ile Ala Leu Asp Asn Ser Thr Phe Lys Ala Ser Ala Thr Gly
        195                 200                 205

Leu Gly Gly Thr Asp Gln Lys Ile Asp Gly Asp Leu Lys Phe Asp Asp
    210                 215                 220

Thr Thr Gly Lys Tyr Tyr Ala Lys Val Thr Val Thr Gly Gly Thr Gly
225                 230                 235                 240

Lys Asp Gly Tyr Tyr Glu Val Ser Val Asp Lys Thr Asn Gly Glu Val
                245                 250                 255

Thr Leu Ala Gly Gly Ala Thr Ser Pro Leu Thr Gly Gly Leu Pro Ala
            260                 265                 270

Thr Ala Thr Glu Asp Val Lys Asn Val Gln Val Ala Asn Ala Asp Leu
        275                 280                 285

Thr Glu Ala Lys Ala Ala Leu Thr Ala Ala Gly Val Thr Gly Thr Ala
    290                 295                 300

Ser Val Val Lys Met Ser Tyr Thr Asp Asn Asn Gly Lys Thr Ile Asp
305                 310                 315                 320

Gly Gly Leu Ala Val Lys Val Gly Asp Asp Tyr Tyr Ser Ala Thr Gln
                325                 330                 335

Asn Lys Asp Gly Ser Ile Ser Ile Asn Thr Thr Lys Tyr Thr Ala Asp
            340                 345                 350

Asp Gly Thr Ser Lys Thr Ala Leu Asn Lys Leu Gly Gly Ala Asp Gly
        355                 360                 365
```

```
Lys Thr Glu Val Val Ser Ile Gly Gly Lys Thr Tyr Ala Ala Ser Lys
    370                 375                 380

Ala Glu Gly His Asn Phe Lys Ala Gln Pro Asp Leu Ala Glu Ala Ala
385                 390                 395                 400

Ala Thr Thr Thr Glu Asn Pro Leu Gln Lys Ile Asp Ala Ala Leu Ala
                405                 410                 415

Gln Val Asp Thr Leu Arg Ser Asp Leu Gly Ala Val Gln Asn Arg Phe
                420                 425                 430

Asn Ser Ala Ile Thr Asn Leu Gly Asn Thr Val Asn Asn Leu Thr Ser
            435                 440                 445

Ala Arg Ser Arg Ile Glu Asp Ser Asp Tyr Ala Thr Glu Val Ser Asn
450                 455                 460

Met Ser Arg Ala Gln Ile Leu Gln Gln Ala Gly Thr Ser Val Leu Ala
465                 470                 475                 480

Gln Ala Asn Gln Val Pro Gln Asn Val Leu Ser Leu Leu Arg
                485                 490
```

<210> SEQ ID NO 2
<211> LENGTH: 271
<212> TYPE: PRT
<213> ORGANISM: Salmonella enterica

<400> SEQUENCE: 2

```
Ala Gln Val Ile Asn Thr Asn Ser Leu Ser Leu Leu Thr Gln Asn Asn
  1               5                  10                  15

Leu Asn Lys Ser Gln Ser Ala Leu Gly Thr Ala Ile Glu Arg Leu Ser
             20                  25                  30

Ser Gly Leu Arg Ile Asn Ser Ala Lys Asp Asp Ala Ala Gly Gln Ala
         35                  40                  45

Ile Ala Asn Arg Phe Thr Ala Asn Ile Lys Gly Leu Thr Gln Ala Ser
     50                  55                  60

Arg Asn Ala Asn Asp Gly Ile Ser Ile Ala Gln Thr Thr Glu Gly Ala
 65                  70                  75                  80

Leu Asn Glu Ile Asn Asn Asn Leu Gln Arg Val Arg Glu Leu Ala Val
                 85                  90                  95

Gln Ser Ala Asn Ser Thr Asn Ser Gln Ser Asp Leu Asp Ser Ile Gln
            100                 105                 110

Ala Glu Ile Thr Gln Arg Leu Asn Glu Ile Asp Arg Val Ser Gly Gln
        115                 120                 125

Thr Gln Phe Asn Gly Val Lys Val Leu Ala Gln Asp Asn Thr Leu Thr
    130                 135                 140

Ile Gln Val Gly Ala Asn Asp Gly Glu Thr Ile Asp Ile Asp Leu Lys
145                 150                 155                 160

Gln Ile Asn Ser Gln Thr Leu Gly Leu Asp Thr Leu Asn Gly Ala Ala
                165                 170                 175

Gly Ala Thr Thr Thr Glu Asn Pro Leu Gln Lys Ile Asp Ala Ala Leu
            180                 185                 190

Ala Gln Val Asp Thr Leu Arg Ser Asp Leu Gly Ala Val Gln Asn Arg
        195                 200                 205

Phe Asn Ser Ala Ile Thr Asn Leu Gly Asn Thr Val Asn Asn Leu Thr
    210                 215                 220

Ser Ala Arg Ser Arg Ile Glu Asp Ser Asp Tyr Ala Thr Glu Val Ser
225                 230                 235                 240

Asn Met Ser Arg Ala Gln Ile Leu Gln Gln Ala Gly Thr Ser Val Leu
                245                 250                 255
```

Ala Gln Ala Asn Gln Val Pro Gln Ser Val Leu Ser Leu Leu Arg
        260                 265                 270

<210> SEQ ID NO 3
<211> LENGTH: 1488
<212> TYPE: DNA
<213> ORGANISM: Salmonella enterica

<400> SEQUENCE: 3
atggcacaag tcattaatac aaacagcctg tcgctgttga cccagaataa cctgaacaaa     60
tcccagtccg ctctgggcac cgctatcgag cgtctgtctt ccggtctgcg tatcaacagc    120
gcgaaagacg atgcggcagg tcaggcgatt gctaaccgtt ttaccgcgaa catcaaaggt    180
ctgactcagg cttcccgtaa cgctaacgac ggtatctcca ttgcgcagac cactgaaggc    240
gcgctgaacg aaatcaacaa caacctgcag cgtgtgcgtg aactggcggt tcagtctgct    300
aacagcacca actcccagtc tgacctcgac tccatccagg ctgaaatcac ccagcgcctg    360
aacgaaatcg accgtgtatc cggccagact cagttcaacg gcgtgaaagt cctggcgcag    420
gacaacaccc tgaccatcca ggttggtgcc aacgacggtg aaactatcga tatcgatctg    480
aagcagatca actctcagac cctgggtctg atacgctga atgtgcaaca aaatataag     540
gtcagcgata cggctgcaac tgttacagga tatgccgata ctacgattgc tttagacaat    600
agtacttta aagcctcggc tactggtctt ggtggtactg accagaaaat tgatggcgat    660
ttaaaatttg atgatacgac tggaaaatat tacgccaaag ttaccgttac ggggggaact    720
ggtaaagatg ctattatga gtttccgtt gataagacga acggtgaggt gactcttgct     780
ggcggtgcga cttccccgct tacaggtgga ctacctgcga cagcaactga ggatgtgaaa    840
aatgtacaag ttgcaaatgc tgatttgaca gaggctaaag ccgcattgac agcagcaggt    900
gttaccggca cagcatctgt tgttaagatg tcttatactg ataataacgg taaaactatt    960
gatggtggtt tagcagttaa ggtaggcgat gattactatt ctgcaactca aaataaagat   1020
ggttccataa gtattaatac tacgaaatac actgcagatg acggtacatc caaaactgca   1080
ctaaacaaac tgggtggcgc agacggcaaa accgaagttg tttctattgg tgtaaaaact   1140
tacgctgcaa gtaaagccga aggtcacaac tttaaagcac agcctgatct ggcggaagcg   1200
gctgctacaa ccaccgaaaa cccgctgcag aaaattgatg ctgctttggc acaggttgac   1260
acgttacgtt ctgacctggg tgcggtacag aaccgtttca actccgctat taccaacctg   1320
ggcaacaccg taaacaacct gacttctgcc cgtagccgta tcgaagattc cgactacgcg   1380
accgaagttt ccaacatgtc tcgcgcgcag attctgcagc aggccggtac ctccgttctg   1440
gcgcaggcga accaggttcc gcaaaacgtc ctctctttac tgcgttaa              1488

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
agcagactga accgccag                                                   18

<210> SEQ ID NO 5
<211> LENGTH: 19
<212> TYPE: DNA
<213> ORGANISM: Artificial Sequence

```
<220> FEATURE:
<223> OTHER INFORMATION: primer

<400> SEQUENCE: 5
gctacaacca ccgaaaacc                                                19

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
aacccgctgc agaaaattg                                                19

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
caggactttc acgccgtt                                                 18

<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8
cttcagatcg atatcgatag tttcac                                        26

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
attcagcgta tccagacc                                                 18

<210> SEQ ID NO 10
<211> LENGTH: 27
<212> TYPE: DNA
<213> ORGANISM: Artiificial Sequence
<220> FEATURE:
<223> OTHER INFORMATION: primer

<400> SEQUENCE: 10
gttccgcaaa gcgtcctctc tttactg                                       27

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
cagtaaagag aggacgcttt gcggaac                                       27
```

<210> SEQ ID NO 12
<211> LENGTH: 31
<212> TYPE: DNA
<213> ORGANISM: Artificial Sequence
<220> FEATURE:
<223> OTHER INFORMATION: primer

<400> SEQUENCE: 12
ggtgcagctg gagctacaac caccgaaaac c    31

<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13
ggtgcagctg gaaacccgct gcagaaaatt g    31

<210> SEQ ID NO 14
<211> LENGTH: 819
<212> TYPE: DNA
<213> ORGANISM: Salmonella enterica

<400> SEQUENCE: 14
atggcacaag tcattaatac aaacagcctg tcgctgttga cccagaataa cctgaacaaa     60
tcccagtccg ctctgggcac cgctatcgag cgtctgtctt ccggtctgcg tatcaacagc    120
gcgaaagacg atgcggcagg tcaggcgatt gctaaccgtt ttaccgcgaa catcaaaggt    180
ctgactcagg cttcccgtaa cgctaacgac ggtatctcca ttgcgcagac cactgaaggc    240
gcgctgaacg aaatcaacaa caacctgcag cgtgtgcgtg aactggcggt tcagtctgct    300
aacagcacca actcccagtc tgacctcgac tccatccagg ctgaaatcac ccagcgcctg    360
aacgaaatcg accgtgtatc cggccagact cagttcaacg gcgtgaaagt cctggcgcag    420
gacaacaccc tgaccatcca ggttggtgcc aacgacggtg aaactatcga tatcgatctg    480
aagcagatca actctcagac cctgggtctg gatacgctga atggtgctgc tggtgctaca    540
accaccgaaa accgctgca gaaaattgat gctgctttgg cacaggttga cacgttacgt    600
tctgacctgg gtgcggtaca gaaccgtttc aactccgcta ttaccaacct gggcaacacc    660
gtaaacaacc tgacttctgc ccgtagccgt atcgaagatt ccgactacgc gaccgaagtt    720
tccaacatgt ctcgcgcgca gattctgcag caggccggta cctccgttct ggcgcaggcg    780
aaccaggttc gcaaagcgt cctctctttta ctgcgttaa    819

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
agcaccattc agcgtatcca gacc    24

<210> SEQ ID NO 16
<211> LENGTH: 24
<212> TYPE: DNA
<213> ORGANISM: Artificial Sequence
<220> FEATURE:
<223> OTHER INFORMATION: primer

```
<400> SEQUENCE: 16
gctggtgcta caaccaccga aaac                                              24

<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
tcgagatatc ctgtaacagt tgcagcc                                           27

<210> SEQ ID NO 18
<211> LENGTH: 29
<212> TYPE: DNA
<213> ORGANISM: Artificial Sequence
<220> FEATURE:
<223> OTHER INFORMATION: primer

<400> SEQUENCE: 18
actcgaggac ggtacatcca aaactgcac                                         29

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
cgtcatccat ggcgaactg                                                    19

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
gcttctttgc agctccttcg t                                                 21

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
ttttgggatg gaattggaca c                                                 21

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
tgcaggtgaa gccttcaacc                                                   20

<210> SEQ ID NO 23
```

```
<211> LENGTH: 20
<212> TYPE: DNA
<213> ORGANISM: Artificial Sequence
<220> FEATURE:
<223> OTHER INFORMATION: primer

<400> SEQUENCE: 23
ccctcaacgg aagaaccaaa                                               20

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
cacatcaggt acgatccagg c                                             21

<210> SEQ ID NO 25
<211> LENGTH: 253
<212> TYPE: PRT
<213> ORGANISM: Salmonella enterica

<400> SEQUENCE: 25
```

Ala Gln Val Ile Asn Thr Asn Ser Leu Ser Leu Leu Thr Gln Asn Asn
 1               5                  10                  15

Leu Asn Lys Ser Gln Ser Ala Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ala Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ala Val
                85                  90                  95

Gln Ser Ala Asn Ser Thr Asn Ser Gln Ser Asp Leu Asp Ser Ile Gln
            100                 105                 110

Ala Glu Ile Thr Gln Arg Leu Asn Glu Ile Asp Arg Val Ser Gly Gln
        115                 120                 125

Thr Gln Phe Asn Gly Val Lys Val Leu Ala Gln Asp Asn Thr Leu Thr
    130                 135                 140

Ile Gln Val Gly Ala Asn Asp Gly Glu Thr Ile Asp Ile Asp Leu Lys
145                 150                 155                 160

Gly Ala Ala Gly Asn Pro Leu Gln Lys Ile Asp Ala Ala Leu Ala Gln
                165                 170                 175

Val Asp Thr Leu Arg Ser Asp Leu Gly Ala Val Gln Asn Arg Phe Asn
            180                 185                 190

Ser Ala Ile Thr Asn Leu Gly Asn Thr Val Asn Asn Leu Thr Ser Ala
        195                 200                 205

Arg Ser Arg Ile Glu Asp Ser Asp Tyr Ala Thr Glu Val Ser Asn Met
    210                 215                 220

Ser Arg Ala Gln Ile Leu Gln Gln Ala Gly Thr Ser Val Leu Ala Gln
225                 230                 235                 240

Ala Asn Gln Val Pro Gln Ser Val Leu Ser Leu Leu Arg
                245                 250

<210> SEQ ID NO 26
<211> LENGTH: 230
<212> TYPE: PRT
<213> ORGANISM: Salmonella enterica

<400> SEQUENCE: 26

Ala Gln Val Ile Asn Thr Asn Ser Leu Ser Leu Leu Thr Gln Asn Asn
1               5                   10                  15

Leu Asn Lys Ser Gln Ser Ala Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ala Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ala Val
                85                  90                  95

Gln Ser Ala Asn Ser Thr Asn Ser Gln Ser Asp Leu Asp Ser Ile Gln
            100                 105                 110

Ala Glu Ile Thr Gln Arg Leu Asn Glu Ile Asp Arg Val Ser Gly Gln
        115                 120                 125

Thr Gln Phe Asn Gly Val Lys Val Leu Gly Ala Ala Gly Asn Pro Leu
    130                 135                 140

Gln Lys Ile Asp Ala Ala Leu Ala Gln Val Asp Thr Leu Arg Ser Asp
145                 150                 155                 160

Leu Gly Ala Val Gln Asn Arg Phe Asn Ser Ala Ile Thr Asn Leu Gly
                165                 170                 175

Asn Thr Val Asn Asn Leu Thr Ser Ala Arg Ser Arg Ile Glu Asp Ser
            180                 185                 190

Asp Tyr Ala Thr Glu Val Ser Asn Met Ser Arg Ala Gln Ile Leu Gln
        195                 200                 205

Gln Ala Gly Thr Ser Val Leu Ala Gln Ala Asn Gln Val Pro Gln Ser
    210                 215                 220

Val Leu Ser Leu Leu Arg
225                 230

<210> SEQ ID NO 27
<211> LENGTH: 192
<212> TYPE: PRT
<213> ORGANISM: Salmonella enterica

<400> SEQUENCE: 27

Ala Gln Val Ile Asn Thr Asn Ser Leu Ser Leu Leu Thr Gln Asn Asn
1               5                   10                  15

Leu Asn Lys Ser Gln Ser Ala Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ala Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ala Val
                85                  90                  95

Gln Ser Ala Gly Ala Ala Gly Asn Pro Leu Gln Lys Ile Asp Ala Ala

```
              100                 105                 110
Leu Ala Gln Val Asp Thr Leu Arg Ser Asp Leu Gly Ala Val Gln Asn
            115                 120                 125

Arg Phe Asn Ser Ala Ile Thr Asn Leu Gly Asn Thr Val Asn Asn Leu
        130                 135                 140

Thr Ser Ala Arg Ser Arg Ile Glu Asp Ser Asp Tyr Ala Thr Glu Val
145                 150                 155                 160

Ser Asn Met Ser Arg Ala Gln Ile Leu Gln Gln Ala Gly Thr Ser Val
                165                 170                 175

Leu Ala Gln Ala Asn Gln Val Pro Gln Ser Val Leu Ser Leu Leu Arg
            180                 185                 190

<210> SEQ ID NO 28
<211> LENGTH: 765
<212> TYPE: DNA
<213> ORGANISM: Salmonella enterica

<400> SEQUENCE: 28
atggcacaag tcattaatac aaacagcctg tcgctgttga cccagaataa cctgaacaaa      60
tcccagtccg ctctgggcac cgctatcgag cgtctgtctt ccggtctgcg tatcaacagc     120
gcgaaagacg atgcggcagg tcaggcgatt gctaaccgtt ttaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggtgcc aacgacggtg aaactatcga tatcgatctg     480
aagggtgcag ctggaaaccc gctgcagaaa attgatgctg ctttggcaca ggttgacacg     540
ttacgttctg acctgggtgc ggtacagaac cgtttcaact ccgctattac caacctgggc     600
aacaccgtaa acaacctgac ttctgcccgt agccgtatcg aagattccga ctacgcgacc     660
gaagtttcca acatgtctcg cgcgcagatt ctgcagcagg ccggtacctc cgttctggcg     720
caggcgaacc aggttccgca agcgtcctc tctttactgc gttaa                      765

<210> SEQ ID NO 29
<211> LENGTH: 696
<212> TYPE: DNA
<213> ORGANISM: Salmonella enterica

<400> SEQUENCE: 29
atggcacaag tcattaatac aaacagcctg tcgctgttga cccagaataa cctgaacaaa      60
tcccagtccg ctctgggcac cgctatcgag cgtctgtctt ccggtctgcg tatcaacagc     120
gcgaaagacg atgcggcagg tcaggcgatt gctaaccgtt ttaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctgggtgca     420
gctggaaacc cgctgcagaa aattgatgct gctttggcac aggttgacac gttacgttct     480
gacctgggtg cggtacagaa ccgtttcaac tccgctatta ccaacctggg caacaccgta     540
aacaacctga cttctgcccg tagccgtatc gaagattccg actacgcgac cgaagtttcc     600
```

```
aacatgtctc gcgcgcagat tctgcagcag gccggtacct ccgttctggc gcaggcgaac    660
caggttccgc aaagcgtcct ctctttactg cgttaa                              696

<210> SEQ ID NO 30
<211> LENGTH: 582
<212> TYPE: DNA
<213> ORGANISM: Salmonella enterica

<400> SEQUENCE: 30
atggcacaag tcattaatac aaacagcctg tcgctgttga cccagaataa cctgaacaaa     60
tcccagtccg ctctgggcac cgctatcgag cgtctgtctt ccggtctgcg tatcaacagc    120
gcgaaagacg atgcggcagg tcaggcgatt gctaaccgtt ttaccgcgaa catcaaaggt    180
ctgactcagg cttcccgtaa cgctaacgac ggtatctcca ttgcgcagac cactgaaggc    240
gcgctgaacg aaatcaacaa caacctgcag cgtgtgcgtg aactggcggt tcagtctgct    300
ggtgcagctg gaaacccgct gcagaaaatt gatgctgctt tggcacaggt tgacacgtta    360
cgttctgacc tgggtgcggt acagaaccgt ttcaactccg ctattaccaa cctgggcaac    420
accgtaaaca acctgacttc tgcccgtagc cgtatcgaag attccgacta cgcgaccgaa    480
gtttccaaca tgtctcgcgc gcagattctg cagcaggccg gtacctccgt tctggcgcag    540
gcgaaccagg ttccgcaaag cgtcctctct ttactgcgtt aa                       582

<210> SEQ ID NO 31
<211> LENGTH: 4
<212> TYPE: PRT
<213> ORGANISM: Artificial Sequence
<220> FEATURE:
<223> OTHER INFORMATION: Linker

<400> SEQUENCE: 31

Gly Ala Ala Gly
 1

<210> SEQ ID NO 32
<211> LENGTH: 4
<212> TYPE: PRT
<213> ORGANISM: Artificial Sequence
<220> FEATURE:
<223> OTHER INFORMATION: Linker

<400> SEQUENCE: 32

Lys Glu Lys Glu
 1

<210> SEQ ID NO 33
<211> LENGTH: 12
<212> TYPE: DNA
<213> ORGANISM: Artificial Sequence
<220> FEATURE:
<223> OTHER INFORMATION: primer fragment

<400> SEQUENCE: 33
ggtgcagctg ga                                                         12

<210> SEQ ID NO 34
<211> LENGTH: 8
<212> TYPE: PRT
<213> ORGANISM: Salmonella enterica
```

```
<400> SEQUENCE: 34

Gln Arg Val Arg Glu Leu Ala Val
  1               5

<210> SEQ ID NO 35
<211> LENGTH: 8
<212> TYPE: PRT
<213> ORGANISM: Salmonella enterica

<400> SEQUENCE: 35

Asp Thr Val Lys Val Lys Ala Thr
  1               5
```

IMMUNOADJUVANT FLAGELLIN-BASED COMPOUNDS AND USE THEREOF

CROSS-REFERENCE TO RELATED APPLICATIONS

This application is filed pursuant to 35 USC 371 as a United States National Phase Application of International Patent Application Serial No. PCT/EP2009/057836 filed on Jun. 23, 2009, which claims the priority of EP 08305327.2 filed on Jun. 25, 2008 in Europe which are incorporated herein in their entirety.

FIELD OF THE INVENTION

The present invention relates to induction and/or stimulation of the immune response in an individual or an animal.

It concerns in particular new immunoadjuvant compounds, useful for immunogenic and vaccine compositions.

BACKGROUND OF THE INVENTION

The development of safe and efficacious vaccines remains a major goal in global public health.

In particular, vaccines termed "mucosal" have emerged as an attractive potential alternative to injectable vaccines.

Mucosal administration has many potentially desirable attributes. Perhaps the most compelling reason for developing mucosal vaccine delivery techniques is development of a first line of immunity defense, by generating local immunity at the mucosal site of entry for many invading pathogens.

Moreover some investigators have reported that a common mucosal immune system exists, whereby mucosal immunity induced at one site can lead to immunity at a distal mucosal site (McGhee, J. R. et al. The mucosal immune system: from fundamental concepts to vaccine development. Vaccine 1992, 10:75-88).

In addition, delivery of an antigen via a mucosal site has the potential to generate a systemic immune response as well.

This suggests that significant benefits can be achieved by the delivering of vaccines in a non-invasive way, e.g. intranasally or other mucosal route, to elicit immunity to a wide range of pathogens that may enter at different mucosal sites.

The majority of the present day vaccines (mucosal vaccines or other) are composed of two main components: (i) the target antigen of therapeutic interest and (ii) immunoadjuvant compound(s) that stimulate and/or induce immunogenicity against said antigen.

The nature of known immunoadjuvants varies greatly, but includes in particular mineral oils, bacterial extracts, live and attenuated organisms and suspensions of aluminum hydroxide metals.

Even if adjuvants provide enhance immune responses, their use can also elicit adverse side effects, function notably of their administered route. Therefore, the numbers of adjuvants that are approved and effective in humans remain relatively limited.

Advances in the field of innate immunity have provided a better understanding of both the cellular and molecular mechanisms governing the regulation of the host immune response.

This better knowledge of immune system has allowed the research and development of new potential useful immunoadjuvants.

In particular, toll-like receptors (TLRs) are instrumental in the coordinated induction of innate and adaptive immunity in mammals. Since TLRs are expressed by a broad variety of cell types, they are able to trigger immunity throughout the body.

Following infection by pathogenic microorganisms, TLRs recognize conserved motifs referred to as microbe-associated molecular patterns (MAMPs). TLR engagement induces a gene expression program dedicated to both innate clearance of and acquired immunity to pathogenic microorganisms. For instance, TLRs induce the production of chemokines which, in turn, specifically attract the polymorphonuclear neutrophils (PMNs) directly involved in innate microbial clearance. Furthermore, TLRs promote the secretion of pleiotropic immune mediators (such as TNFα) and the functional maturation of dendritic cells (DCs) which specialize in antigen presentation to lymphocytes.

Consequently, TLR agonists not only stimulate "broadly specific" pro-inflammatory immune responses but also enhance the adaptive immune response to defined antigens, and are thus considered to be immunoadjuvants.

Despite these potentially beneficial effects, the systemic toxicity of MAMPs has prompted efforts to develop derivatives that bias MAMP activity towards adjuvancy. Indeed, engineering molecules with unique properties is a major challenge in manipulating immune responses.

Bacterial flagellins (the major flagella components in many bacterial pathogens) are specific, unique agonists for TLR5 activation.

The FliC flagellin from *Salmonella enterica* Serovar Typhimurium (*S. Typhimurium*) is the paradigm for studies on flagellum structure-function, immunity and TLR5 signaling.

It is a 494 amino-acid protein with two distinct domains. The amino- and carboxy-terminal "conserved" regions form a domain that is essential for TLR5 activation.

The middle domain of flagellin FliC comprises amino acids not mandatory for TLR5 signaling. It is designated as a "hypervariable" region, since the primary sequences greatly vary in composition and size from one bacterial species to another. In contrast, it is known that the hypervariable region is essential for flagellin antigenicity.

It has been shown that intravenous (i.v.) injection of flagellins promotes a systemic response, characterized by the production of pro-inflammatory mediators (such as TNFα or IL-6) and DC activation.

Furthermore, flagellins trigger mucosa-specific innate and adaptive defense mechanisms. For instance, epithelial cell lines and lung mucosa upregulate the production of chemokines like CXCL8 (IL-8) and CCL20 which, in turn, recruit mucosal PMNs and DCs, respectively.

Various authors have also reported that flagellins are potent systemic and mucosal immunoadjuvants that elicit (i) serum and/or secretory antibody responses and (ii) Th1 and Th2 cell responses to both the flagellins themselves and co-administered antigens.

Due to their potent systemic and mucosal immunoadjuvant activities, flagellins may be particularly interesting for the development of vaccine, and in particular of mucosal vaccine type.

However, most of the said flagellin-type adjuvants are not completely suitable for such vaccine application, and in particular for said mucosal vaccine strategy.

Indeed, the known flagellin adjuvants show major side effects, and in particular intrinsic antigenic activity and systemic pro-inflammatory properties when administered in vivo.

Moreover, most of the known flagellin-type immunoadjuvants need to be physically linked to the target antigen, in order to elicit a potent immune response when administered in vivo. This requirement obliges supplementary complex manipulations to obtain a suitable flagellin-antigen linkage, and the final useful immunogenic substance.

There is thus a need for new compounds which could be used as immunological adjuvants, in particular to induce and/or to enhance mucosal immune response against an antigen, notably without triggering any significant systemic inflammation side effect.

These new compounds should also, advantageously, be able to trigger an immune response by a simple mixture with the target antigen.

The present invention proposes then new immunoadjuvant compounds that satisfy this need, and which can be particularly useful for the production of immunogenic compositions and of vaccine (in particular of mucosal type).

SUMMARY OF THE INVENTION

It as been found, according to the invention, novel peptide compounds derived from flagellin originating from *Salmonella enterica* Serovar *Typhimurium* of SEQ ID No 1 type, that exhibit an in vivo immune adjuvant activity as illustrated in the examples herein.

It has been also shown according to the present invention that these novel adjuvant compounds exhibit in particular mucosal adjuvant properties, without exerting significant systemic pro-inflammatory effects.

The said new flagellin-derived compounds of the invention are thus particularly useful as immunoadjuvant substances, advantageously to induce and/or to enhance a mucosal immune response.

The present invention thus relates to an immunoadjuvant compound comprising:

a) a N-terminal peptide having at least 90% amino acid identity with the amino acid sequence starting from the amino acid residue located at position 1 of SEQ ID No 1 and ending at an amino acid residue selected from the group consisting of any one of the amino acid residues located at positions 99 to 173 of SEQ ID No 1; and b) a C-terminal peptide having at least 90% amino acid identity with the amino acid sequence starting at an amino acid residue selected from the group consisting of any one of the amino acid residues located at positions 401 to 406 of SEQ ID No 1 and ending at the amino acid residue located at position 494 of SEQ ID No 1, wherein:
the said N-terminal and C-terminal peptides are directly linked one to the other, or
the said N-terminal and C-terminal peptides are indirectly linked, one to the other, through a spacer chain.

Preferred embodiments of the immunoadjuvant compound of the invention are defined hereafter in the description.

The invention also relates to a pharmaceutical composition comprising an immunoadjuvant compound as defined above (or in the following description), together with one or more pharmaceutically acceptable excipients.

The pharmaceutical composition according to the invention comprises an immunoadjuvant compound as defined above, together with one or more antigens.

The said pharmaceutical composition is thus advantageously an immunogenic composition (i.e. a composition which aims at inducing an immune response against an antigen, e.g. to produce antibodies) or a vaccine composition (i.e. a composition which aims at inducing an immune response in a subject or an animal in order to treat or to prevent a disease).

According to a preferred embodiment, the said immunogenic composition or the said vaccine advantageously comprises the said immunoadjuvant compound of the invention which is not covalently linked to the said one or more antigens.

The present invention also relates to the immunoadjuvant compound as defined above, for use as a medicament (in particular to induce and/or to enhance mucosal adjuvant activity).

This invention also concerns the use of an immunoadjuvant compound according to the invention, for manufacturing a pharmaceutical composition, in particular for inducing and/or for enhancing an immune response against one or more antigens other than a flagellin protein (in particular in the mucosal compartment after administration by mucosal route).

This invention also relates to (i) a nucleic acid encoding the immunoadjuvant peptide compound as above disclosed, (ii) a recombinant vector comprising, inserted therein, the said nucleic acid, (iii) a host cell transfected or transformed with the said nucleic acid or with the said recombinant vector.

(A) A schematic 3D view of the recombinant flagellins.

The structure of wild type flagellin FliC is presented in the left-hand panel using Pymol. In the monomer, terminal regions (1-170 and 400-494) are tightly folded in α-helixes and form a structural domain involved in flagellum function. The motif 89-96 (black) is essential for TLR5 signaling. The FliC "hypervariable" domain is mainly constituted of β structures and β turns.

Using Swiss-Model, and overall structure was predicted for $FliC_{\Delta204\text{-}292}$ and $FliC_{\Delta174\text{-}400}$, showing partial and total deletion of the hypervariable region, respectively.

For $FliC_{\Delta191\text{-}352}$, the positions of amino acids delineating the deletion are shown on the left-hand panel. $FliC_{\Delta174\text{-}400}$ and $FliC_{\Delta191\text{-}352}$ contain GAAG SEQ ID No. 31 and LELE SEQ ID No. 32 linkers at the deletion junction, respectively.

(B, C) Cross-reactivity of FliC-specific sera.

Hyperimmune sera were obtained after s.c. administration of flagellin formulated with CFA for priming, followed by IFA boosts. Serum was titrated in ELISAs for FliC, $FliC_{\Delta204\text{-}292}$, $FliC_{\Delta191\text{-}352}$, and $FliC_{\Delta174\text{-}400}$. The results are representative of 2 experiments. (B) Cross-reactivity of anti-FliC serum. (C) Cross-reactivity of anti-$FliC_{\Delta174\text{-}400}$ serum.

Statistical significance ($p>0.05$ in a Mann-Whitney test) is indicated by an asterisk.

Figure 2:
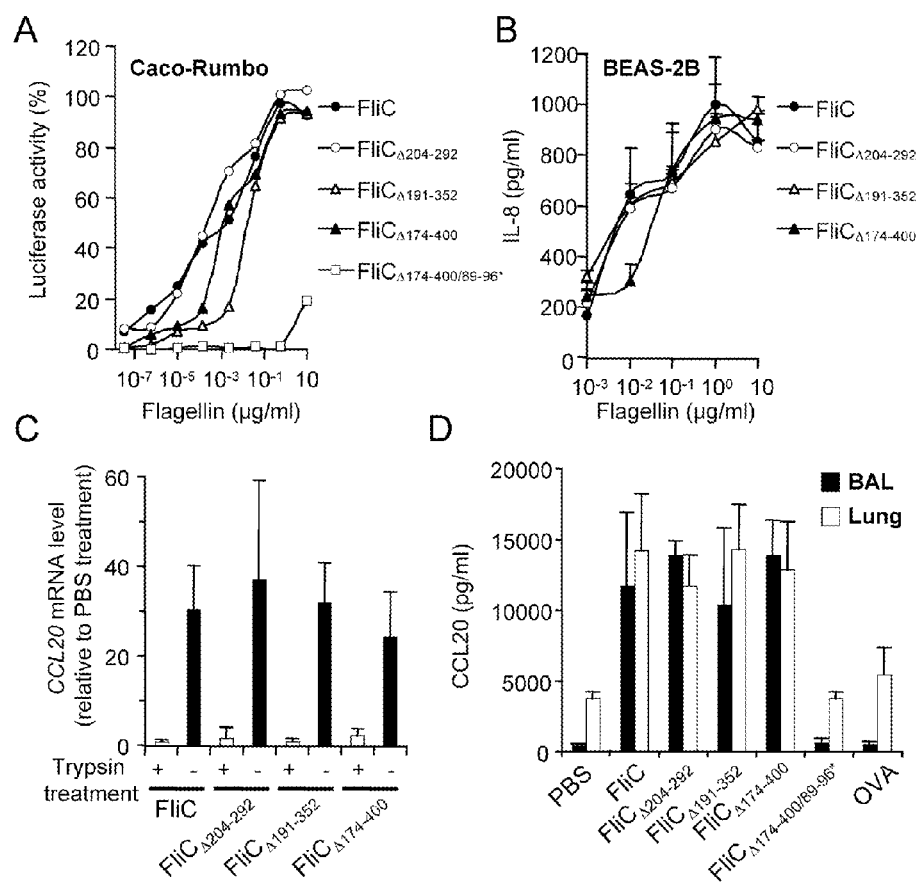

FIG. 2. Epithelial and mucosal pro-inflammatory activity of hypervariable region-deleted flagellins.

(A, B) Activation of epithelial cells by recombinant flagellins.

Human epithelial cells were activated with flagellins FliC, $FliC_{\Delta204\text{-}292}$, $FliC_{\Delta191\text{-}352}$, $FliC_{\Delta174}\text{-}400$ or $FliC_{\Delta174\text{-}400/89\text{-}96*}$ at the indicated concentrations. Caco-Rumbo cells harboring the reporter fusion CCL20-luc were activated for 6 h and luciferase activity was normalized to the maximal activity measured with saturating FliC levels (A). BEAS-2B bronchial epithelial cells were stimulated for 16 h before measuring IL-8 levels in the supernatant. Results are representative of 1 of 2 independent experiments (B).

(C-D) Stimulation of the mucosal innate response by deleted flagellins.

Recombinant flagellins or trypsin-treated preparations (1 μg equivalent) were administered i.n. to anesthetized mice (n=3-5). CCL20-specific mRNA levels in the whole lungs were determined 2 h later using real time qRT-PCR (C). Six hours after instillation, BALs (black bars) and lungs (open bars) were sampled to measure the CCL20 concentration (D).

Statistical significance (p>0.05) was determined in a Mann-Whitney test.

Figure 3:
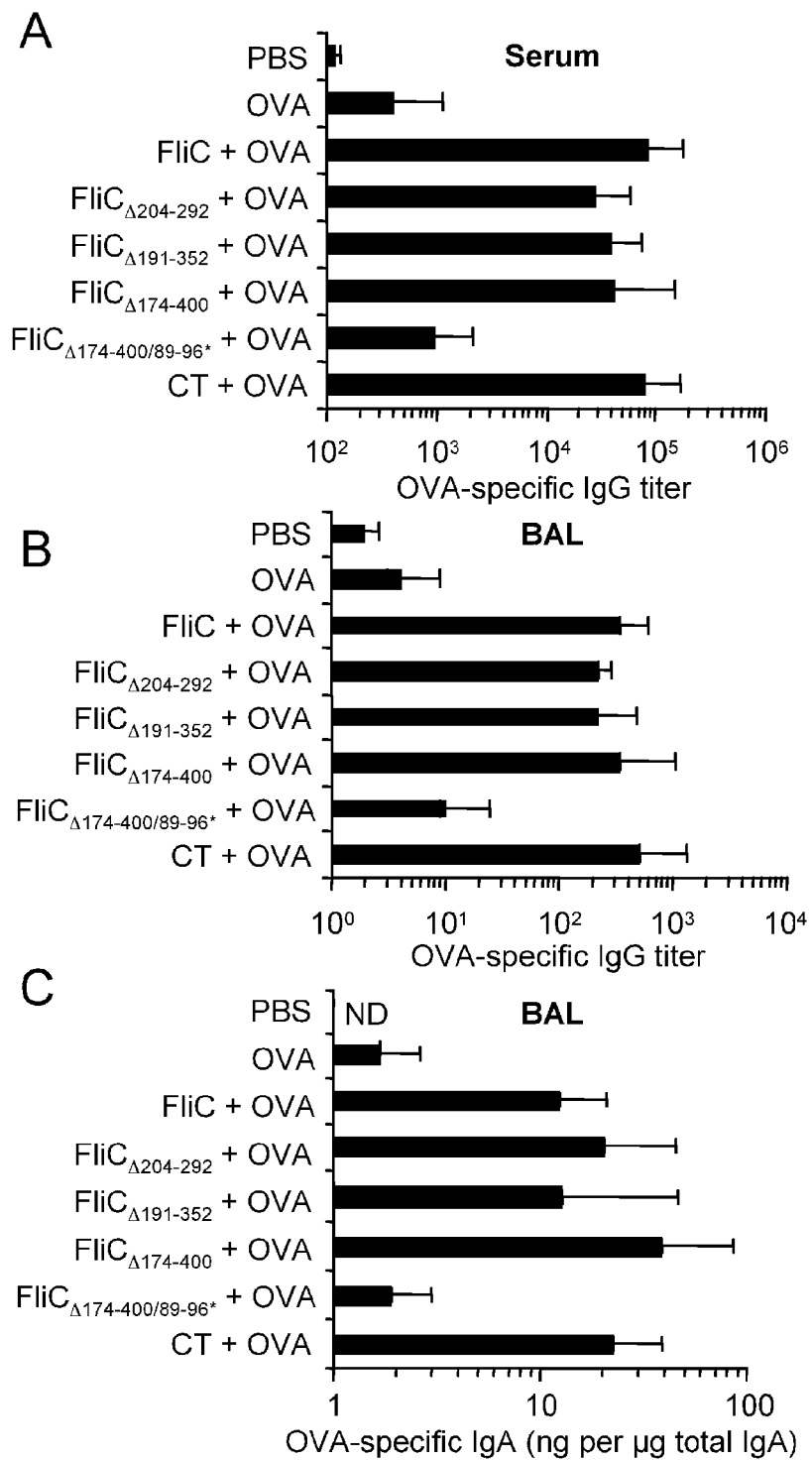

FIG. 3. Adjuvant effect of flagellins with hypervariable region deletion.

Mice (n=8) were immunized i.n. with ovalbumin (OVA) ±flagellins or cholera toxin (CT) on days 1 and 21.

On day 35, OVA-specific IgG titers were measured in the serum (A) and BALs (B).

The concentration of OVA-specific IgA in BALs was determined (C).

Results are representative of 1 of 2 independent experiments. Statistical significance (p>0.05) was determined in a Mann-Whitney test.

Figure 4:
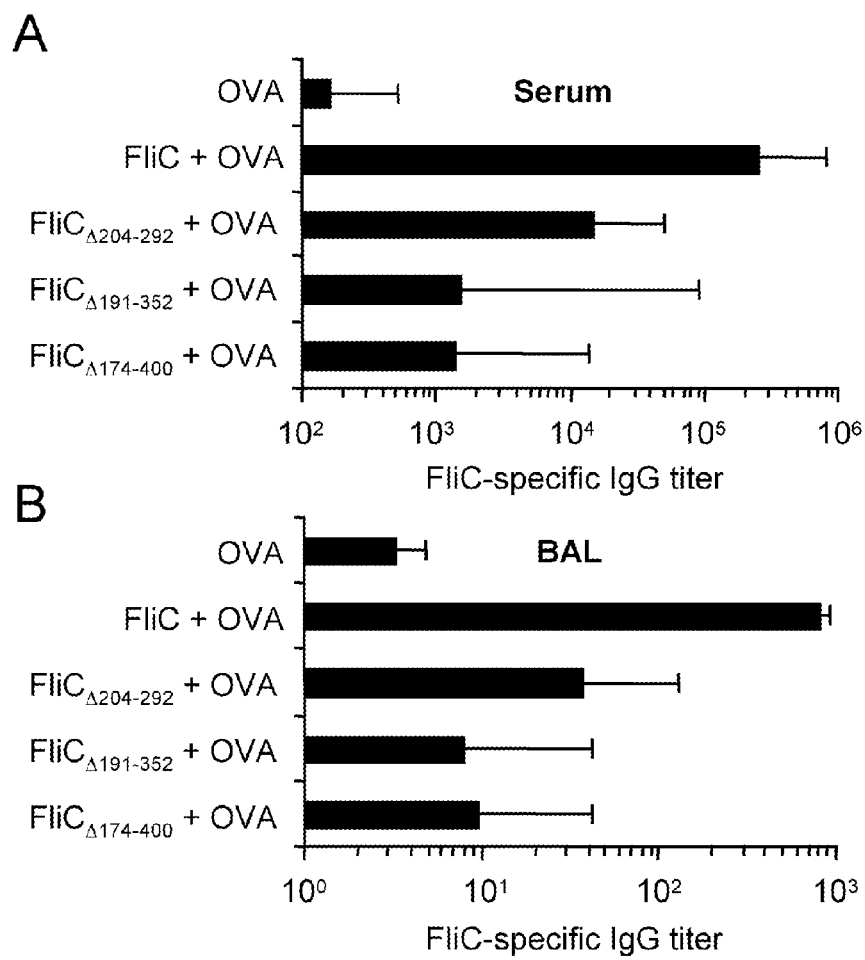

FIG. 4. Intrinsic antigenic properties of flagellins lacking a hypervariable region.

Mice (n=8) were immunized i.n. with ovalbumin (OVA) ±flagellins or cholera toxin (CT) or LPS on days 1 and 21.

On day 35, FliC-specific IgG titers were measured in the serum (A) and BALs (B). Results are representative of 1 of 2 independent experiments.

Statistical significance (p>0.05) was determined in a Mann-Whitney test.

Figure 5:
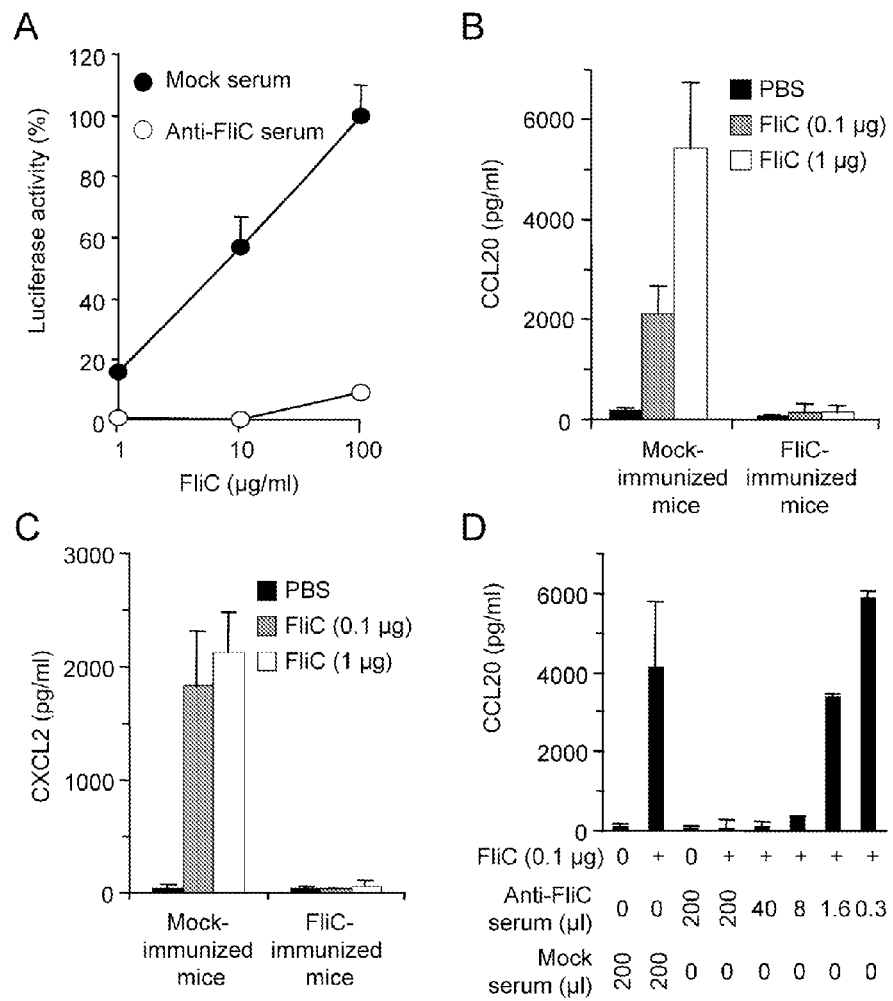

FIG. 5. Neutralization of TLR5 signaling by flagellin-specific antibodies.

NMRI mice were immunized s.c. at week 1 with 1 μg flagellin FliC and CFA, followed by boosts at weeks 3, 5, 7 with FliC and IFA. In mock conditions, animals were similarly treated with ovalbumin and adjuvants or adjuvants alone. Experiments were carried out at week 9.

(A) In vitro TLR5-neutralizing activity of flagellin-specific immune serum.

Caco-Rumbo epithelial cells harboring the reporter construct CCL20-luc were activated for 6 h with the flagellin FliC incubated with 50% v/v FliC hyper-immune (open circles) or mock (black circles) sera. Luciferase activity was determined and normalized to the activity obtained with 100 ng/ml FliC. Results are representative of 1 of 3 independent experiments.

(B, C) In vivo TLR5-neutralizing activity of flagellin-specific immune serum.

Immunized animals (n=3) were injected i.v. with PBS (black bars) or 0.1 μg (grey bars) or 1 μg of flagellin FliC (open bars). Sera were collected 2 h later and the concentrations of CCL20 (B) and CXCL2 (C) were determined by ELISA.

(D) The neutralizing activity of immune serum.

Animals (n=3 per dose) were passively transferred i.v. with various amounts of flagellin-specific or mock serum, and treated 1 h later i.v. with recombinant flagellins, as indicated. Chemokine production in serum 2 h post-challenge was measured by ELISA.

Statistical significance (p>0.05) was determined using a Mann-Whitney test.

Figure 6:
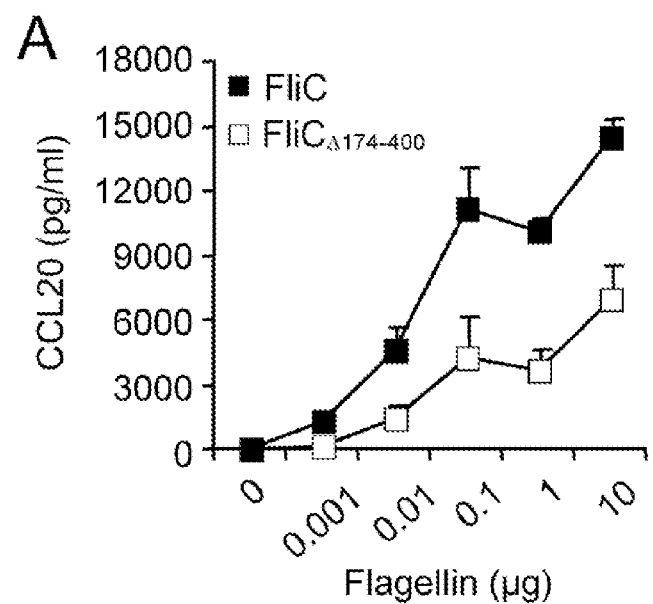
Figure 6:
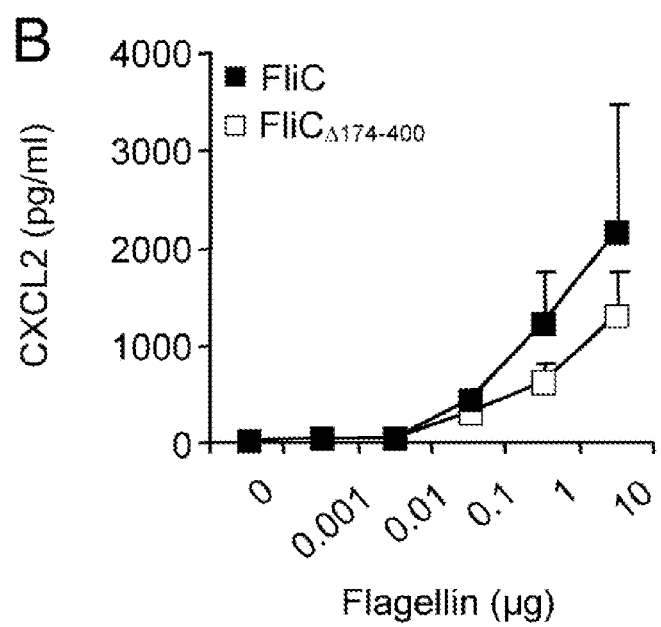

FIG. 6. Intranasal dose-response activity of flagellins FliC and $FliC_{\Delta 174\text{-}400}$.

Mice (n=3-5) were instilled i.n. with various amounts of flagellins FliC (black squares) or $FliC_{\Delta 174\text{-}400}$ (open squares). The concentrations of CCL20 (A) and CXCL2 (B) were determined 6 h later in BALs using an ELISA.

Statistical significance (p>0.05) was determined in a Mann-Whitney U test.

Figure 7:
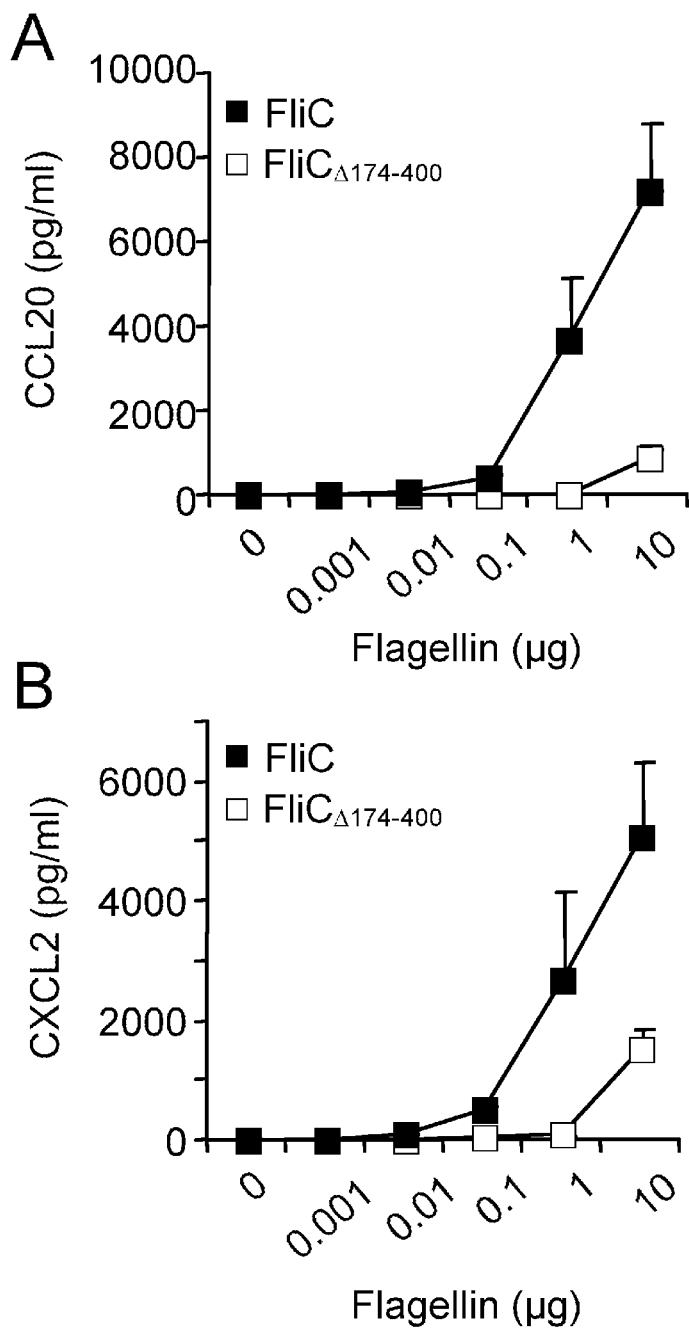

FIG. 7. Alteration of the systemic activation ability of hypervariable region-deleted flagellin $FliC_{\Delta 174\text{-}400}$.

Various amounts of flagellin FliC (black squares) or $FliC_{\Delta 174\text{-}400}$ (open squares) were administered i.v. The concentrations of CCL20 (A) and CXCL2 (B) were determined 2 h later in the serum using an ELISA.

Statistical significance (p>0.05) was determined in a Mann-Whitney test.

Figure 8:
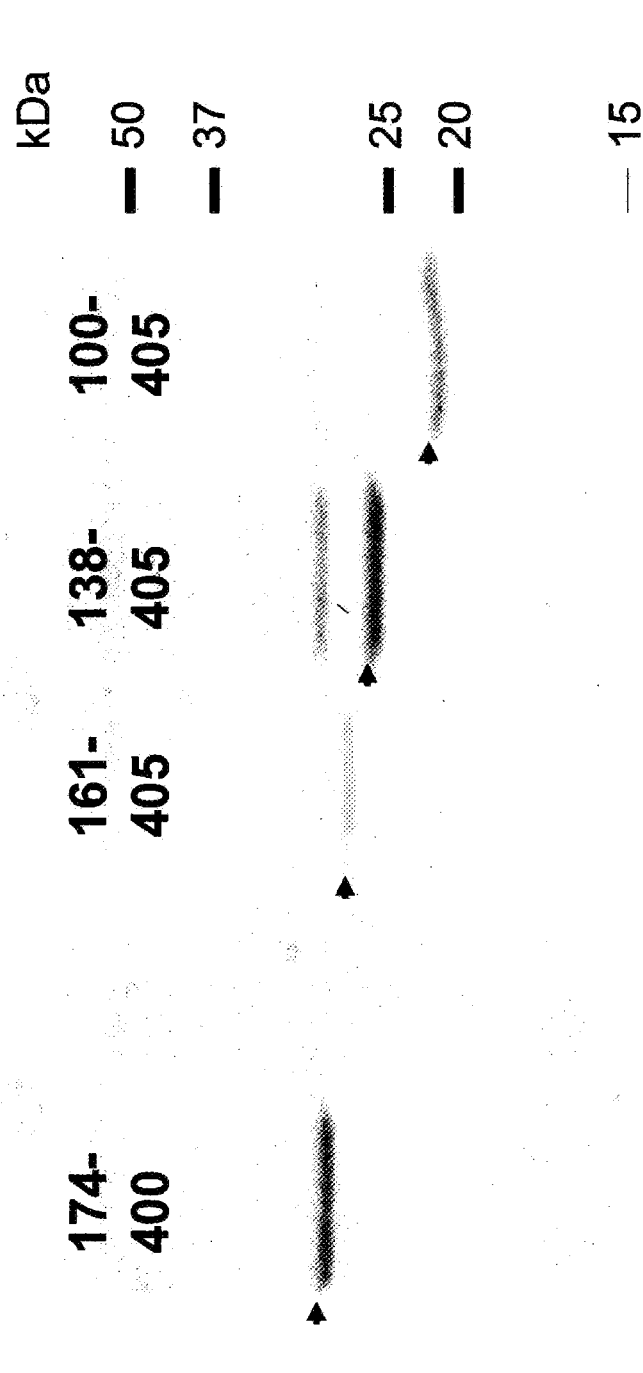

FIG. 8: SDS PAGE analysis of various recombinant hypervariable region-deleted flagellins FIG. 8 consists of a photograph of a SDS PAGE electrophoresis of recombinantly produced $FliC_{\Delta 174\text{-}400}$, $FliC_{\Delta 161\text{-}405}$, $FliC_{\Delta 138\text{-}405}$ and $FliC_{\Delta 100\text{-}405}$ after staining with Coomassie blue.

Figure 9:
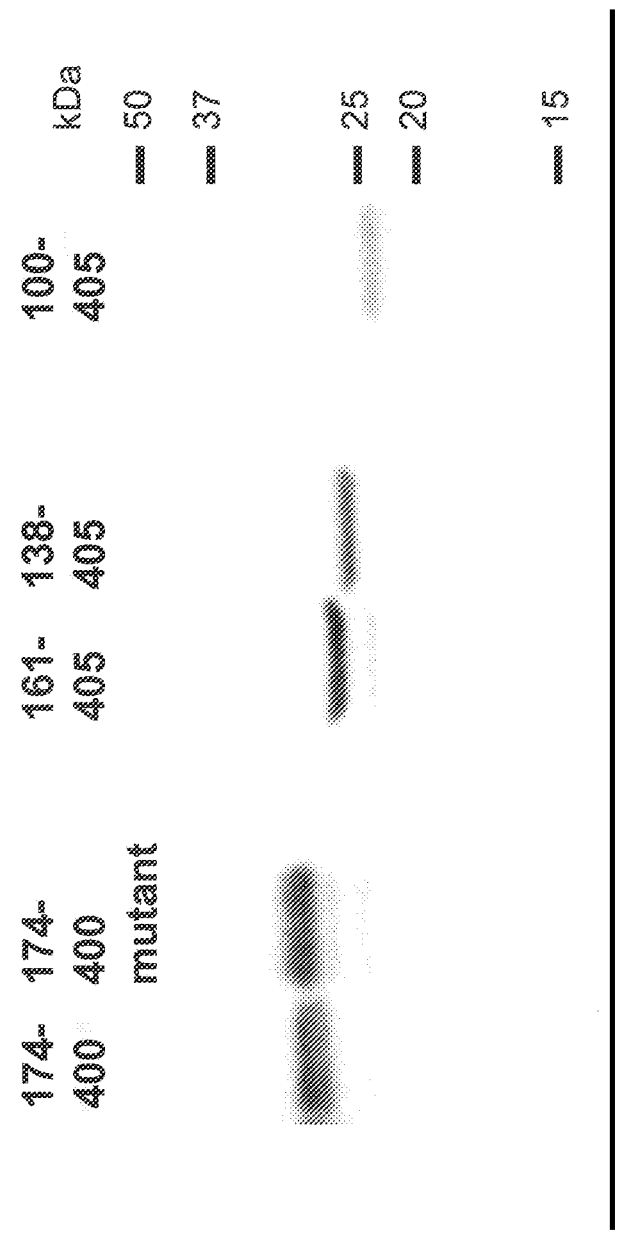

FIG. 9: Immunoblot analysis of various recombinant hypervariable region-deleted flagellins FIG. 9 consists of a photograph of a Western blot electrophoresis of recombinantly produced $FliC_{\Delta 174\text{-}400}$, $FliC_{\Delta 161\text{-}405}$, and $FliC_{\Delta 138\text{-}405}$ and $FliC_{\Delta 100\text{-}405}$ after staining with anti-FliC antibodies.

Figure 10:
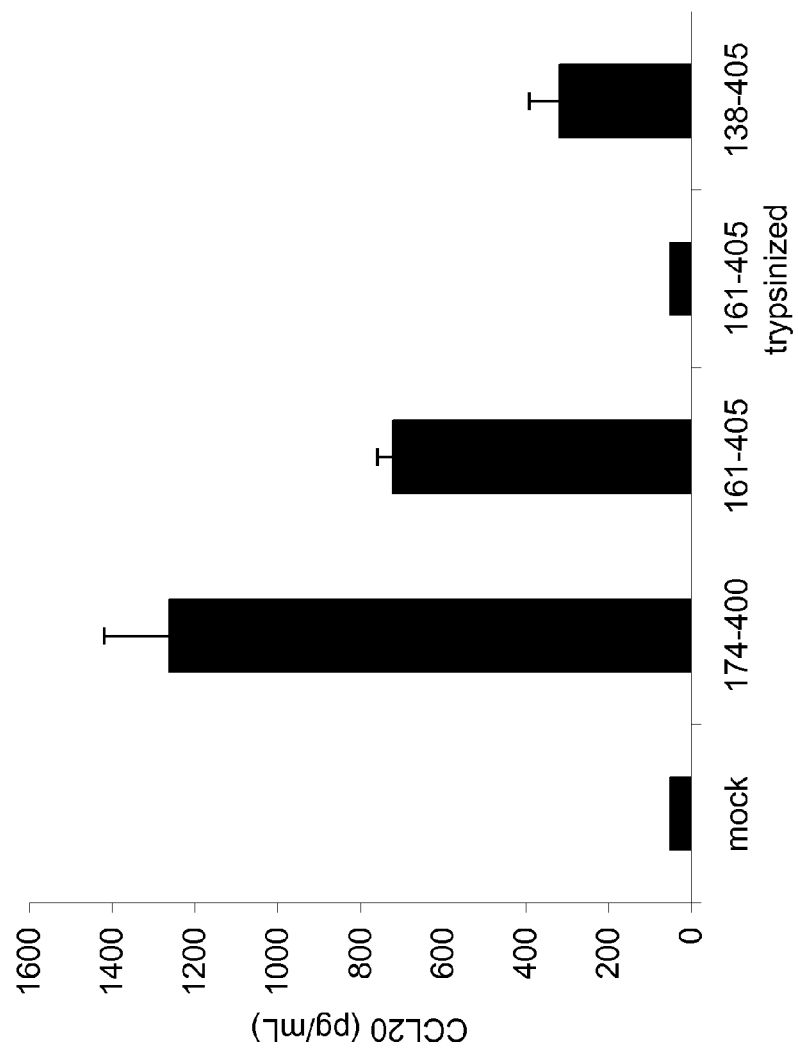

FIG. 10: Induction of CCL20 chemokine production by various recombinant hypervariable region-deleted flagellins Stimulation of the systemic innate response by deleted flagellins.

Recombinant flagellins or trypsin-treated preparations (10 μg equivalent) were administered i.p. to mice (n=2). Two hours after injection, serum were sampled to measure the CCL20 concentration.

Figure 11:
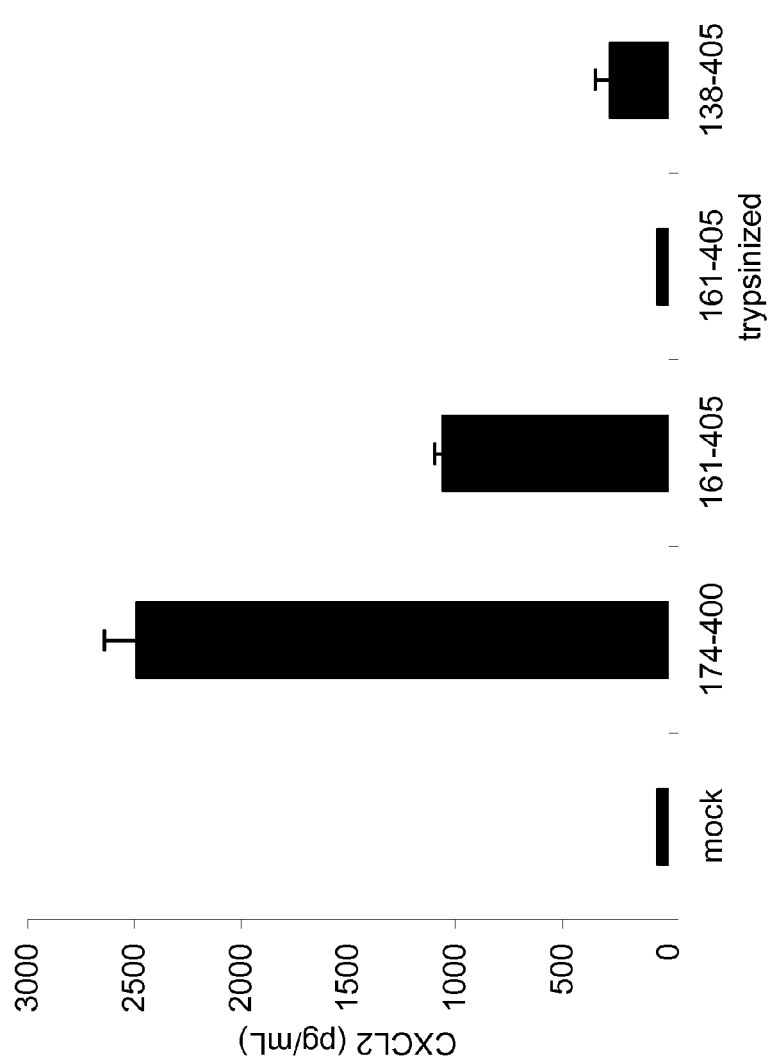

FIG. 11: Induction of CXCL2 chemokine production induction by various recombinant hypervariable region-deleted flagellins Stimulation of the systemic innate response by deleted flagellins.

Recombinant flagellins or trypsin-treated preparations (10 μg equivalent) were administered i.p. to mice (n=2). Two hours after injection, serum were sampled to measure the CXCL2 concentration.

Figure 12:
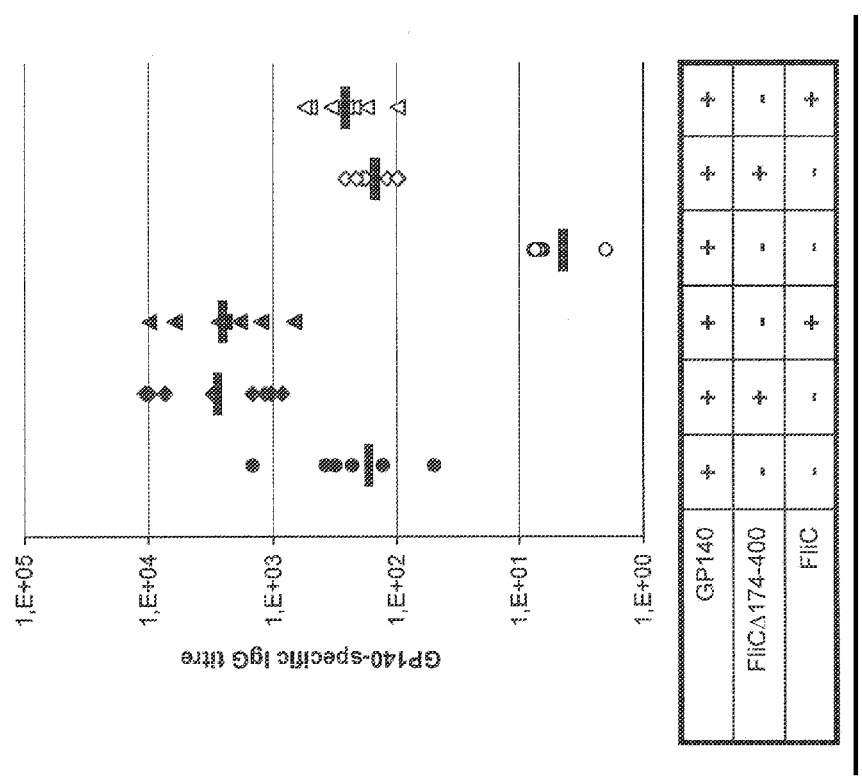

FIG. 12: Adjuvant effect of recombinant $FliC_{\Delta 174\text{-}400}$ for immunisation against the gp140 antigen from the HIV virus.

Mice (n=6) were immunized i.n. with gp140 (5 μg)±flagellins (1 μg) on days 1 and 21.

On day 35, gpP140-specific IgG titers were measured in the serum (closed symbols) and BALs (open symbols). Results are representative of 1 of 2 independent experiments.

Figure 13:
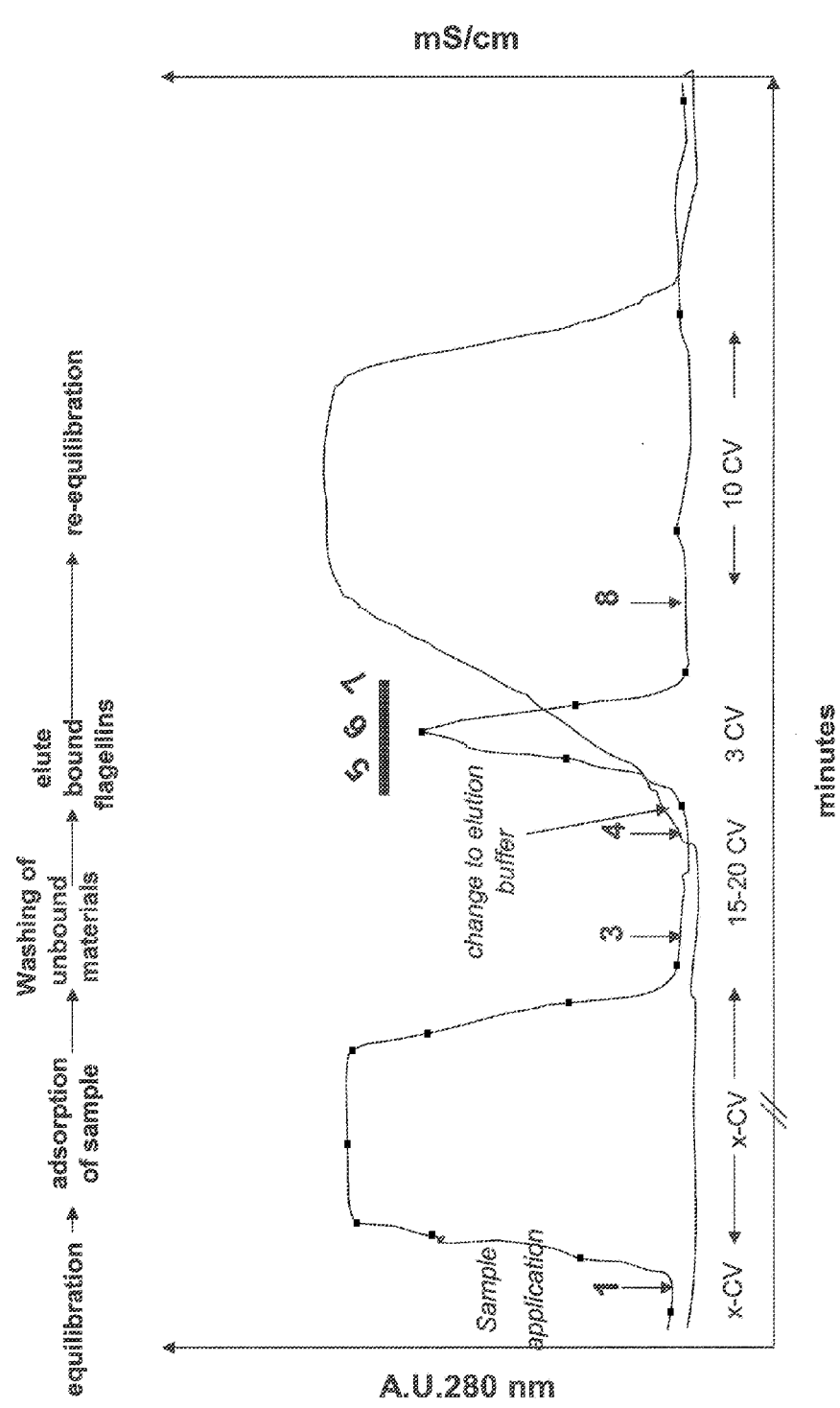

FIG. 13: Chromatography profile at 280 nm of a purification cycle of FliC on an immunoaffinity substrate onto which anti-$FliC_{\Delta 174\text{-}400}$ mouse monoclonal antibodies have been immobilized.

Figure 14:
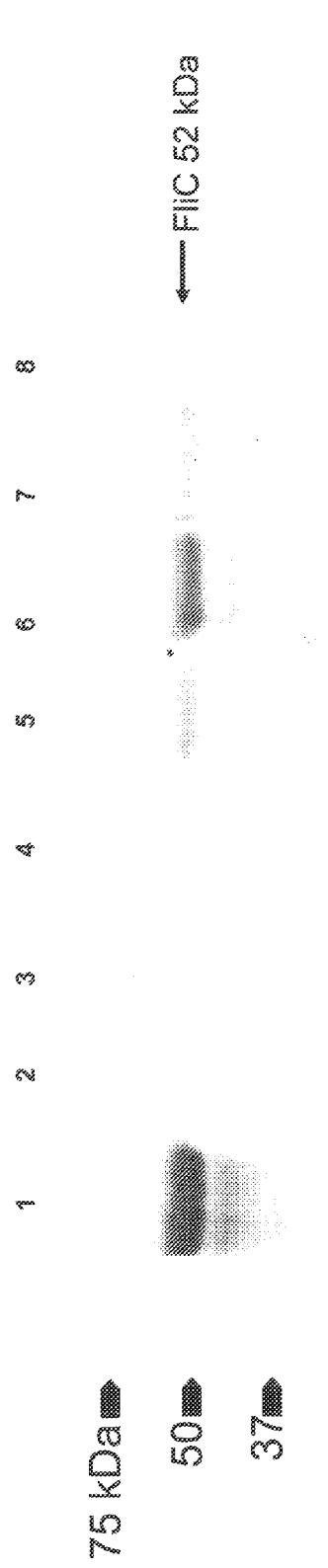

FIG. 14: Electrophoresis analysis of various chromatography fractions collected during a purification cycle of FliC on an immunoaffinity substrate onto which anti-$FliC_{\Delta 174\text{-}400}$ mouse monoclonal antibodies have been immobilized FIG. 14 consists of a photograph of a SDS PAGE electrophoresis of fractions collected as depicted in FIG. 13 after staining with Coomassie blue.

DETAILED DESCRIPTION OF THE INVENTION

According to the present invention novel compounds have been shown to induce an in vivo mucosal immunoadjuvant activity allowing the induction of an immune response against a target antigen, when the said novel compounds are administered with the suitable corresponding antigen(s).

Notably, it has been shown herein that the novel adjuvant compounds of the invention exert their immunoadjuvant properties also after intranasal administration to mice. The said immunoadjuvant compounds of the invention are thus able to potentiate systemic and mucosal immune response.

It has also been demonstrated that the said flagellin-derived immunoadjuvant compound of the invention has TLR5-mediated mucosal adjuvant properties, with in vivo mucosa pro-inflammatory effect, but do not shows any significant systemic pro-inflammatory side effect after systemic injection.

Moreover, the results contained in the examples herein show that the said flagellin-derived immunoadjuvant compound does not show significant intrinsic antigenic effect, i.e. the molecule of interest prevents or attenuates the potency to trigger flagellin-specific antibodies, notably into serum or bronchoalveolar lavage (BAL) when administered by intranasal route.

The above results show that the said flagellin-derived immunoadjuvant compound of the invention may be used as an effective adjuvant of the immune response, especially for inducing mucosal immune responses.

The said peptide compound can thus be useful notably when it is comprised in (i) a mucosal vaccine compositions to prevent or to treat diseases by inducing a mucosal immune response within the subject organism body, or in (ii) an immunogenic composition for enhancing or triggering an immune response against a desired antigen.

In particular, as shown in the Examples herein, the inventors have found that, unexpectedly, TLR5 signaling is compartmentalized, since new particular $FliC_{\Delta174-400}$ flagellin (i.e. a flagellin-derived peptide whereof peptide sequence SEQ ID No 1 from the *Salmonella enterica* Serovar *Typhimurium* ATCC14028 flagellin FliC is deleted from position 174 to position 400) stimulates immunity in the mucosa but is devoid of any significant systemic pro-inflammatory effect.

The inventors have also established that $FliC_{\Delta174-400}$ flagellin has prominent beneficial properties, due to its poor capacity to generate neutralizing fliC-specific antibodies.

In addition, it has been found herein that $FliC_{\Delta174-400}$ flagellin is strongly attenuated for systemic signaling compared with wild type flagellin, whereas mucosal activity was unaffected.

It has also been shown herein that other hyervariable region-deleted flagellins, including $FliC_{\Delta161-405}$, and $FliC_{\Delta138-405}$ are endowed with immunoadjuvant properties.

Immunoadjuvant Peptides of the Invention

The findings allow the inventors to design a peptide family, which should have the same properties and advantages as $FliC_{\Delta174-400}$, $FliC_{\Delta161-405}$, and $FliC_{\Delta138-405}$ flagellins.

The said peptide family is defined starting from $FliC_{\Delta174-400}$, $FliC_{\Delta161-405}$, and $FliC_{\Delta138-405}$ flagellins studied in the Examples herein, and based on flagellin peptide sequence SEQ ID No 1 and on the crystallographic structure of the peptide, to predict truncated versions that could have remaining TLR5-stimulating activity.

The present invention relates thus advantageously to the immunoadjuvant compound comprising:

a) a N-terminal peptide having an amino acid sequence starting from the amino acid residue located at position 1 of SEQ ID No 1 and ending at an amino acid residue selected from the group consisting of any one of the amino acid residues located at positions 99 to 173 of SEQ ID No 1; and b) a C-terminal peptide having an amino acid sequence starting at an amino acid residue selected from the group consisting of any one of the amino acid residues located at positions 401 to 406 of SEQ ID No 1 and ending at the amino acid residue located at position 494 of SEQ ID No 1, wherein:

the said C-terminal peptide is directly linked to the N-terminal peptide, or the said N-terminal peptide and the C-terminal peptide are indirectly linked, one to the other, through an intermediate spacer chain.

Comprises/comprising and grammatical variations thereof when used in this specification are to be taken to specify the presence of stated features, integers, steps or components or groups thereof, but do not preclude the presence or addition of one or more other features, integers, steps, components or groups thereof.

The compound of the invention may be interchangeably termed herein "immunoadjuvant compound" or "flagellin-derived peptide".

By "immunoadjuvant compound", it is understood that the flagellin-derived peptide of the invention can induce and/or enhance the immune response against an antigen when administered to a subject or an animal.

It is also intended to mean a substance that acts generally to accelerate, prolong, or enhance the quality of specific immune responses to a specific antigen.

As described therein, the said immunoadjuvant compound can be used in a vaccine or immunogenic composition, together with one or more antigens and pharmaceutically acceptable excipients.

The peptide sequence of SEQ ID No 1 above-mentioned is originating from the *Salmonella enterica* Serovar *Typhimurium* ATCC14028 flagellin FliC (accession number AAL20871).

Polypeptide numbering starts at the first amino-acid after the eventual N-terminal methionine (not shown in SEQ ID No 1), which is typically excised by methionine aminopeptidase in bacteria host cells as under-mentioned.

The N-terminal and C-terminal peptides of the flagellin-derived peptide of the invention have advantageously at least 90%, and even more, amino acid identity with the corresponding amino acid sequence portion of SEQ ID No 1.

Descriptions of identity and how this may be determined are well known to those skilled in the art.

As intended herein, a given amino acid sequence of interest possesses 90% or more identity with a reference amino acid sequence when the said amino acid sequence of interest possesses at least 90%, 91%, 92%, 93%, 94%, 95%, 69%, 97%, 98%, 99% or 99.5% amino acid identity with the said reference amino acid sequence.

To determine the percent of identity between two amino acid sequences, the sequences are aligned for optimal comparison purposes. For example, gaps can be introduced in one or both of a first and a second amino acid sequence for optimal alignment and non-homologous sequences can be disregarded for comparison purposes.

For optimal comparison purposes, the percent of identity of two amino acid sequences can be achieved with CLUSTAL W (version 1.82) with the following parameters: (1) CPU MODE=ClustalW mp; (2) ALIGNMENT=<<full>>; (3) OUTPUT FORMAT=<<aln w/numbers>>; (4) OUTPUT ORDER=<<aligned>>; (5) COLOR ALIGNMENT=<<no>>; (6) KTUP (word size)=<<default>>; (7) WINDOW LENGTH=<<default>>; (8) SCORETYPE=<<percent>>;

(9) TOPDIAG=<<default>>; (10) PAIRGAP=<<default>>; (11) PHYLOGENETIC TREE/TREE TYPE=<<none>>; (12) MATRIX=<<default>>; (13) GAP OPEN=<<default>>; (14) END GAPS=<<default>>; (15) GAP EXTENSION=<<default>>; (16) GAP DISTANCES=<<default>>; (17) TREE TYPE=<<cladogram>>et (18) TREE GRAP DISTANCES=<<hide>>.

In particular, it is understood that minor modifications can be made without destroying the advantages and activity of the flagellin-derived peptide of the invention.

Such modifications are included within the meaning of the terms "immunoadjuvant compound" or "flagellin-derived peptide" of the invention so long as the particular immune activity are preserved, in particular the TLR5-mediated mucosal adjuvant properties without any significant systemic pro-inflammatory side effect.

Further, various molecules can be attached, covalently or not covalently, to the flagellin-derived peptide of the invention, including for example, other polypeptides, carbohydrates, nucleic acids or lipids.

These attached molecules consist eventually in the antigen against which the immune response is sought. Such modifications are included within the definition of the invention.

Minor modifications can also concern, for example, conservative substitutions of naturally occurring amino acids and as well as structural alterations which incorporate non-naturally occurring amino acids, amino acid analogs and functional mimetics. For example, a Lysine amino acid residue is considered to be a conservative substitution for the Arginine amino acid residue.

Thus, as intended herein, a first polypeptide having at least 90% amino acid identity with a second polypeptide of reference encompass first polypeptides comprising one or more amino acid differences as compared to the second polypeptide of reference and wherein the said amino acid differences are selected from the group consisting of (i) one or more amino acid substitutions, (ii) one or more amino acid deletions and (iii) one or more amino acid additions, or any combination of (i), (ii) and (iii).

Generally, the invention thus encompass variant polypeptides having one or more amino acid substitutions, deletions or additions, as compared to a polypeptide of reference, preferably 1, 2, 3, 4, 5, 6, 7, 8, 9, or 10 amino acid substitutions, and/or 1, 2, 3, 4, 5, 6, 7, 8, 9, or 10 amino acid deletions and/or 1, 2, 3, 4, 5, 6, 7, 8, 9, or 10 amino acid additions as compared to the polypeptide of reference.

Those skills in the art know or can determine what structure constitutes functionally equivalent amino acid analogs and amino acid mimetics.

As above-mentioned, the C-terminal and N-terminal peptides of flagellin-derived peptide of the invention can be directly linked, advantageously covalently by a peptide bond.

In an alternative embodiment, the said N-terminal and C-terminal peptides of the flagellin-derived peptide of the invention are indirectly linked, one to the other, through a spacer chain.

The spacer chain should be chosen so as not to interfere with the biological activity of the final compound and also so that immunogenicity of the final compound is not significantly increased.

The spacer chain is preferably made up of amino acids linked together by peptide bonds, and linked covalently between the N-terminal and C-terminal sequences of the flagellin-derived peptide of the invention. Thus, in preferred embodiments, the spacer chain comprises from 1 to 20 amino acids linked by peptide bonds, wherein the amino acids are selected from the 20 naturally-occurring amino acids. In a more preferred embodiment, the 1 to 20 amino acids are selected from Gly, Ala, Pro, Asn, Gln, Cys, Lys. Even more preferably, the spacer chain is made of NH2-Gly-Ala-Ala-Gly-COOH sequence. SEQ ID No. 31

Non-peptide linkers are also possible: for example, alkyl linkers. These alkyl linkers may further be substituted by any non-sterically hindering group, lower acyl, halogen, CN, $NH_2$, phenyl, etc. Another type of non-peptide linker is a polyethylene glycol group.

The one skill in the art well knows these spacer chains, and can choose the suitable spacer chain, notably depending of the N-terminal peptide and C-terminal peptide sequences he has to link one to the other.

Moreover, the asparagine amino acid residue of the C-terminal sequence, located at amino acid position 488 of SEQ ID No 1, is advantageously replaced by a serine residue.

This substitution has been introduced to mark specifically flagellin-derived peptide of the invention. Such substitution occurs naturally in flagellins of other bacterial species like *Legionnela pneumophila*, without altering the TLR5-stimulating activity. Other substitutions can be introduced in positions that do not alter the adjuvant TLR5-stimulating activity to further mark the flagellin-derived peptide of the invention.

Preferred Embodiments of the Flagellin-Derived Peptide of the Invention

According preferred embodiments, in view of the flagellin peptide sequence SEQ ID No 1 and of the crystallographic structure, the N-terminal peptide of the immunoadjuvant compound of the invention is advantageously selected from the group consisting of the amino acid sequences 1-99, 1-137, 1-160 and 1-173 of SEQ ID No 1.

In particular, the 3D structure of flagellin FliC shows that N-terminal domain is organized in 3 alpha-helixes separated by beta-turns followed by beta-sheets and beta turns. Retaining part(s) of this secondary structures at the N-terminus may be sufficient to retain TLR5-stimulating activity (and in particular mucosal TLR5-stimulating activity), i.e. the amino acid sequences 1-99 of SEQ ID No 1 contains the first 2 alpha-helixes, the amino acid sequences 1-137 of SEQ ID No 1 contains the first 3 alpha-helixes and the amino acid sequences 1-173 of SEQ ID No 1 contains the N-terminal structures found in $FliC_{\Delta 174-400}$ flagellin.

In further preferred embodiments, the said C-terminal peptide of the immunoadjuvant compound is selected from the group consisting of the amino acid sequences 401-494 and 406-494 of SEQ ID No 1.

In particular, the 3D structure of flagellin FliC shows that C-terminal domain is organized in 2 alpha-helixes separated by beta-turns. Retaining part(s) of these secondary structures at the N-terminus may be sufficient to retain TLR5-stimulating activity (and in particular mucosal TLR5-stimulating activity): the amino acid sequences 401-494 of SEQ ID No 1 is the sequence found in $FliC_{\Delta 174-400}$ flagellin whereas the amino acid sequences 406-494 of SEQ ID No 1 contains only the two C-terminal alpha-helixes secondary.

In certain preferred embodiments, the N-terminal peptide of the immunoadjuvant compound of the invention consists of the amino acid sequence starting at the Alanine residue located at position 1 of SEQ ID No 1 and ends at an amino acid residue located at a position of SEQ ID No 1 selected from the group consisting of the amino acid residues located at positions 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172 and 173

In certain preferred embodiments, the C-terminal peptide of the immunoadjuvant compound of the invention consists of the amino acid sequence starting at an amino acid residue located at a position of SEQ ID No 1 selected from the group consisting of the amino acid residues located at positions 401, 402, 403, 404, 405 and 406, and ends at the Arginine residue located at position 494 of SEQ ID No 1.

In a specific aspect of these preferred embodiments, the said N-terminal peptide and the said C-terminal peptide of the immunoadjuvant compound of the invention are advantageously linked, one to the other, through the NH$_2$-Gly-Ala-Ala-Gly-COOH SEQ ID No. 31 above-mentioned spacer chain (i.e. in substitution of the deleted sequence 174-400); the asparagine amino acid residue located at position 488 of SEQ ID No 1 is also advantageously substituted by a serine residue.

Illustrative embodiments of such immunoadjuvant compounds describe above encompass FliC$_{\Delta 174-400}$, FliC$_{\Delta 161-405}$, and FliC$_{\Delta 138-405}$ that are shown in the examples herein; and which are also described in more detail hereunder.

In a yet further embodiment, the said N-terminal and C-terminal peptides of the immunoadjuvant compound of interest consist of the amino acid sequences 1-173 and 401-494 of SEQ ID No 1, respectively.

In a still further embodiment, the said N-terminal and C-terminal peptides of the immunoadjuvant compound of interest consist of the amino acid sequences 1-160 and 406-494 of SEQ ID No 1, respectively.

In a yet further embodiment, the said N-terminal and C-terminal peptides of the immunoadjuvant compound of interest consist of the amino acid sequences 1-137 and 406-494 of SEQ ID No 1, respectively.

In some embodiments, the immunoadjuvant compounds according to the invention comprise an additional methionine residue at their N-terminal end, especially when these compounds are produced as recombinant proteins in bacterial cells.

In the embodiment wherein the said N-terminal and C-terminal peptides of the immunoadjuvant compound of interest consist of the amino acid sequences 1-173 and 401-494 of SEQ ID No 1, the flagellin-derived peptide of the invention consists of the amino acid sequence SEQ ID No 1, deleted from the amino acid sequence extending from amino acid position 174 to amino acid position 400. The flagellin-peptide sequence of the invention is also termed in the present description "FliC$_{\Delta 174-400}$" or "FliC$_{\Delta 174-400}$ flagellin".

According to a preferred embodiment, the said N-terminal peptide and the said C-terminal peptide of the immunoadjuvant compound of the invention are advantageously linked, one to the other, through the NH$_2$-Gly-Ala-Ala-Gly-COOH SEQ ID No. 31 above-mentioned spacer chain (i.e. in substitution of the deleted sequence 174-400); the asparagine amino acid residue located at position 488 of SEQ ID No 1 is also advantageously substituted by a serine residue.

The flagellin-derived peptide of the invention thus obtained is a 271 amino acid sequence, whereof the peptide sequence consists in SEQ ID No 2.

Polypeptide numbering starts at the first amino-acid after the eventual N-terminal methionine (not shown in SEQ ID No 2), which is typically excised by methionine aminopeptidase in bacteria host cells as under-disclosed.

In the embodiment wherein the said N-terminal and C-terminal peptides of the immunoadjuvant compound of interest consist of the amino acid sequences 1-160 and 406-494 of SEQ ID No 1, the flagellin-derived peptide of the invention consists of the amino acid sequence SEQ ID No 1, deleted from the amino acid sequence extending from amino acid position 161 to amino acid position 405. The flagellin-peptide sequence of the invention is also termed in the present description "FliC$_{\Delta 161-405}$" or "FliC$_{\Delta 161-405}$ flagellin".

According to a preferred embodiment, the said N-terminal peptide and the said C-terminal peptide of the immunoadjuvant compound of the invention are advantageously linked, one to the other, through the NH$_2$-Gly-Ala-Ala-Gly-COOH SEQ ID No. 31 above-mentioned spacer chain (i.e. in substitution of the deleted sequence 161-405); the asparagine amino acid residue located at position 488 of SEQ ID No 1 is also advantageously substituted by a serine residue.

The flagellin-derived peptide of the invention thus obtained is a 253 amino acid sequence, whereof the peptide sequence consists in SEQ ID No 25.

Polypeptide numbering starts at the first amino-acid after the eventual N-terminal methionine (not shown in SEQ ID No 25), which is typically excised by methionine aminopeptidase in bacteria host cells as under-disclosed.

In the embodiment wherein the said N-terminal and C-terminal peptides of the immunoadjuvant compound of interest consist of the amino acid sequences 1-137 and 406-494 of SEQ ID No 1, the flagellin-derived peptide of the invention consists of the amino acid sequence SEQ ID No 1, deleted from the amino acid sequence extending from amino acid position 138 to amino acid position 405. The flagellin-peptide sequence of the invention is also termed in the present description "FliC$_{\Delta 138-405}$" or "FliC$_{\Delta 138-405}$ flagellin".

According to a preferred embodiment, the said N-terminal peptide and the said C-terminal peptide of the immunoadjuvant compound of the invention are advantageously linked, one to the other, through the NH$_2$-Gly-Ala-Ala-Gly-COOH SEQ ID No. 31 above-mentioned spacer chain (i.e. in substitution of the deleted sequence 138-405); the asparagine amino acid residue located at position 488 of SEQ ID No 1 is also advantageously substituted by a serine residue.

The flagellin-derived peptide of the invention thus obtained is a 230 amino acid sequence, whereof the peptide sequence consists in SEQ ID No 26.

Polypeptide numbering starts at the first amino-acid after the eventual N-terminal methionine (not shown in SEQ ID No 26), which is typically excised by methionine aminopeptidase in bacteria host cells as under-disclosed.

In the embodiment wherein the said N-terminal and C-terminal peptides of the immunoadjuvant compound of interest consist of the amino acid sequences 1-99 and 406-494 of SEQ ID No 1, the flagellin-derived peptide of the invention consists of the amino acid sequence SEQ ID No 1, deleted from the amino acid sequence extending from amino acid position 100 to amino acid position 405. The flagellin-peptide sequence of the invention is also termed in the present description "FliC$_{\Delta 100-405}$" or "FliC$_{\Delta 100-405}$ flagellin".

According to a preferred embodiment, the said N-terminal peptide and the said C-terminal peptide of the immunoadjuvant compound of the invention are advantageously linked, one to the other, through the NH$_2$-Gly-Ala-Ala-Gly-COOH SEQ ID No. 31 above-mentioned spacer chain (i.e. in substitution of the deleted sequence 100-405); the asparagine amino acid residue located at position 488 of SEQ ID No 1 is also advantageously substituted by a serine residue.

The flagellin-derived peptide of the invention thus obtained is a 192 amino acid sequence, whereof the peptide sequence consists in SEQ ID No 27.

Polypeptide numbering starts at the first amino-acid after the eventual N-terminal methionine (not shown in SEQ ID No 27), which is typically excised by methionine aminopeptidase in bacteria host cells as disclosed below.

Synthesis of the Immunoadjuvant Peptide of the Invention

The flagellin-derived peptide of the invention may be synthesised by recombinant cells obtained by genetic engineering, or by any one of the methods for chemical or enzyme peptide synthesis, that are well known from the one skilled in the art.

1. Synthesis by Recombinant Cells

The flagellin-derived peptide according to the invention may be recombinantly produced by recombinant cells that have been transfected with a nucleic acid that encodes its amino acid sequence and allows its effective production within the transfected cells.

Nucleic Acid Sequence Encoding Flagellin-Derived Peptide of the Invention

The modifications of the said flagellin peptide sequence can be generates using recombinant DNA mutagenesis techniques.

Numerous methods for constructing and modifying DNA sequence, are known to those skilled in the art, and the choice of the said recombinant methods will be known by those skilled in the art.

The "recombinant mutagenesis" techniques comprise, for example, site directed mutagenesis and PCR mutagenesis (see in particular Current Protocols in Molecular Biology, 2007 by John Wiley and Sons, Inc., Chapter 8 and 15).

The said polymerase chain reaction (PCR) is particularly useful for a wide range of mutation procedures and applications. PCR mutagenesis procedures make it possible to modify and engineer any target DNA easily and efficiently. This includes the introduction of, for example, point mutations, deletions or insertions.

These techniques are implemented, for example, on the wild type fliC gene of SEQ ID No 3, isolated from the *S. Typhimurium* strains ATCC14028 which encode the flagellin peptide identified by SEQ ID No 1.

In a preferred embodiment, the fliC gene above-mentioned is deleted for a central portion of its length by PCR mutagenesis (see in particular Current Protocols in Molecular Biology, 2007 by John Wiley and Sons, Inc., Chapter 8 and 15), by using suitable primer pairs chosen in function of the desired N-terminal and C-terminal sequences searched for the peptide of the invention.

For example, based on a pBR322-derived plasmid harbouring the said wild type fliC gene of SEQ ID No 3, under the control of its own promoter, the following primer pairs may be used in PCR mutagenesis technique:

SEQ ID No 4 and SEQ ID No 5, for N-terminal and C-terminal peptides consisting of the amino acid sequences 1-99 and 401-494 of SEQ ID No 1, respectively;

SEQ ID No 4 and SEQ ID No 6, for N-terminal and C-terminal peptides consisting of the amino acid sequences 1-99 and 406-494 of SEQ ID No 1, respectively;

SEQ ID No 7 and SEQ ID No 5, for N-terminal and C-terminal peptides consisting of the amino acid sequences 1-137 and 401-494 of SEQ ID No 1, respectively;

SEQ ID No 7 and SEQ ID No 6, for N-terminal and C-terminal peptides consisting of the amino acid sequences 1-137 and 406-494 of SEQ ID No 1, respectively;

SEQ ID No 8 and SEQ ID No 5, for N-terminal and C-terminal peptides consisting of the amino acid sequences 1-160 and 401-494 of SEQ ID No 1, respectively;

SEQ ID No 8 and SEQ ID No 6, for N-terminal and C-terminal peptides consisting of the amino acid sequences 1-160 and 406-494 of SEQ ID No 1, respectively;

SEQ ID No 9 and SEQ ID No 5, for N-terminal and C-terminal peptides consisting of the amino acid sequences 1-173 and 401-494 of SEQ ID No 1, respectively;

SEQ ID No 9 and SEQ ID No 6, for N-terminal and C-terminal peptides consisting of the amino acid sequences 1-173 and 406-494 of SEQ ID No 1, respectively.

To change the asparagine of position 488 of SEQ ID No 1 into a serine, for example, it can be used site directed-mutagenesis with the following primers SEQ ID No 10 and SEQ ID No 11

To introduce the NH.sub.2-Gly-Ala-Ala-Gly-COOH SEQ ID No. 31 linker at the junction 1-99, 1-137, 1-160 or 1-173 with 401-494 or 406-494 of the flagellin recombinant peptides, the following DNA sequence GGTGCAGCTGGA SEQ ID No. 33 may be added at 5' end of primer sequences SEQ ID No 5 and SEQ ID No 6, giving rise to primers termed, respectively, "F-linker-401" of sequence SEQ ID No 12 and "F-linker-406" of sequence SEQ ID No 13.

The DNA sequence suitable to produce the flagellin derived peptide of the invention $FliC_{\Delta 174-400}$, is for example of sequence SEQ ID 14.

A nucleic acid suitable to produce the flagellin derived peptide of the invention $FliC_{\Delta 161-405}$, is for example of sequence SEQ ID 28.

A nucleic acid suitable to produce the flagellin derived peptide of the invention $FliC_{\Delta 138-405}$, is for example of sequence SEQ ID 29.

A nucleic acid suitable to produce the flagellin derived peptide of the invention $FliC_{\Delta 100-405}$, is for example of sequence SEQ ID 30.

Selection and Use of a Replicable Vector

The nucleic acid sequence disclosed herein, encoding the flagellin-derived peptide of interest, may be inserted into a replicable vector for cloning (amplification of the DNA) or for expression.

Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art.

Vector components generally include, but are not limited to, one or more of a signal sequence if the sequence is to be secreted, an origin of replication, one or more marker genes, an enhancer element, a promoter, and a transcription termination sequence.

Construction of suitable vectors containing one or more of these components employs standard ligation techniques that are known to the skilled artisan.

The flagellin-derived peptide of interest may be produced recombinantly not only directly, but also as a fusion polypeptide with a heterologous polypeptide, which may be a signal sequence or other polypeptide having a specific cleavage site at the N-terminus of the mature protein or peptide. In general, the signal sequence may be a component of the vector, or it may be a part of the DNA encoding the polypeptide of interest that is inserted into the vector. The signal sequence may be a prokaryotic signal sequence selected, for example, from the group of the alkaline phosphatase, penicillinase, Ipp, or heat-stable enterotoxin II leaders. For yeast secretion the signal sequence may be, e.g., the yeast invertase leader, alpha factor leader (including Saccharomyces and Kluyveromyces .alpha.-factor leaders, the latter described in U.S. Pat. No. 5,010,182), or acid phosphatase leader, the C. albicans glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2.mu. plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the nucleic acid encoding the flagellin-derived peptide of interest such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77: 4216 (1980). A suitable selection gene for use in yeast is the trp 1 gene present in the yeast plasmid YRp7. Stinchcomb et al., Nature, 282: 39 (1979); Kingsman et al., Gene, 7: 141 (1979); Tschemper et al, Gene, 10: 157 (1980). The trp1 gene provides a selection marker for a mutant strain of yeast lacking the ability to grow in tryptophan, for example, ATCC No. 44076 or PEP4-1. Jones, Genetics, 85: 12 (1977).

Expression and cloning vectors usually contain a promoter operably linked to the nucleic acid sequence encoding the flagellin-derived peptide to direct mRNA synthesis. Promoters recognized by a variety of potential host cells are well known. Promoters suitable for use with prokaryotic hosts include the beta-lactamase and lactose promoter systems (Chang et al., Nature, 275: 615 (1978); Goeddel et al., Nature, 281: 544 (1979)), alkaline phosphatase, a tryptophan (trp) promoter system (Goeddel, Nucleic Acids Res., 8:4057 (1980); EP 36,776), and hybrid promoters such as the tac promoter (deBoer et al., Proc. Natl. Acad. Sci. USA, 80: 21-25 (1983)). promoters for use in bacterial systems also will contain a Shine-Dalgarno (S.D.) sequence operably linked to the DNA encoding the flagellin-derived peptide of interest.

Examples of suitable promoting sequences for use with yeast hosts include the promoters for 3-phosphoglycerate kinase (Hitzeman et al., J. Biol. Chem., 255: 2073 (1980)) or other glycolytic enzymes (Hess et al., J. Adv. Enzyme Reg., 7: 149 (1968); Holland, Biochemistry, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters that are inducible promoters having the additional advantage of transcription controlled by growth conditions are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Nucleic acid of interest transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus, and Simian Virus 40 (SV40); by heterologous mammalian promoters, e.g., the actin promoter or an immunoglobulin promoter; and by heat-shock promoters, provided such promoters are compatible with the host cell systems.

Transcription of a DNA encoding the flagellin-derived peptide of interest by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the sequence coding for polypeptides of interest, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the flagellin-derived peptide of interest.

Still other methods, vectors, and host cells suitable for adaptation to the synthesis of the flagellin-derived peptide of interest in recombinant vertebrate cell culture are described in Gething et al., Nature, 293: 620-625 (1981); Mantei et al., Nature, 281: 40-46 (1979); EP 117,060; and EP 117,058.

Selection and Transformation of Host Cells

Host cells are transfected or transformed with expression or cloning vectors described herein for flagellin-derived peptide production and cultured in conventional nutrient media modified as appropriate for inducing promoters, selecting transformants, or amplifying the genes encoding the desired sequences.

The culture conditions, such as media, temperature, pH, and the like, can be selected by the skilled artisan without undue experimentation. In general, principles, protocols, and practical techniques for maximizing the productivity of cell cultures can be found in Mammalian Cell Biotechnology: A Practical Approach, M. Butler, ed. (IRL Press, 1991).

Methods of transfection are known to the ordinarily skilled artisan, for example, $CaPO_4$ treatment and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., Gene 23: 315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transformations have been described in U.S. Pat. No. 4,399,216. Transformations into yeast are typically carried out according to the method of Van Solingen et al., J. Bact., 130: 946 (1977) and Hsiao et al., Proc. Natl. Acad. Sci. (USA), 76: 3829 (1979). However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see, Keown et al., Methods in Enzymology, 185: 527-537 (1990) and Mansour et al., Nature, 336: 348-352 (1988).

Suitable host cells for cloning or expressing the DNA in the vectors herein include prokaryote, yeast, or higher eukaryote cells.

Suitable prokaryotes include, but are not limited to, eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325); and K5772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting.

Strain SIN41 of *Salmonella typhimurium* (fliC fljB), is particularly interesting for the production of flagellin-derived peptide, since these prokaryotic host cells do not secrete any flagellins (Proc Natl Acad Sci USA. 2001; 98:13722-7). However flagellins are secreted through specialized secretion system: the so called "Type III secretion system". Interestingly, strain SIN41 produces all components of the type III secretion system required for optimal flagellin secretion. Cloning sequence coding new flagellin peptides under fliC promoter enables secretion in large amounts of the flagellin-derived peptides of interest in strain SIN41.

Strain W3110 is also interesting because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan.sup.r; *E. coli* W3110 strain 37D6, which has the complete genotype tona ptr3 phoA E15 (argF-lac)169 degP ompT rbs7 ilvG kan-.sup.r; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. The *E. coli* strains MG1655, MG1655 ΔfimA-H or MKS12, a fliD- and -fimA-H-deleted MG1655 strain are also interesting candidates for production of recombinant flagellins as secreted proteins (Nat. Biotechnol. 2005; (4):475-81). Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for vectors encoding the flagellin-derived peptide. *Saccharomyces cerevisiae* is a commonly used lower eukaryotic host microorganism.

Others include *Schizosaccharomyces pombe* (Beach and Nurse, Nature, 290: 140 [1981]; EP 139,383 published 2 May 1985); *Kluyveromyces* hosts (U.S. Pat. No. 4,943,529; Fleer et al., Bio/Technology, 9: 968-975 (1991)) such as, e.g., *K. lactis* (MW98-8C, CBS683, CBS4574; Louvencourt et al., J. Bacteriol., 737 [1983]), *K. fragilis* (ATCC 12,424), *K. bulgaricus* (ATCC 16,045), *K. wickeramii*(ATCC 24,178), *K. waltii*(ATCC 56,500), *K. drosophilarum*(ATCC 36,906; Van den Berg et al., Bio/Technology, 8:135 (1990)), *K. thermotolerans*, and *K. marxianus*; *yarrowia* (EP 402, 226); *Pichia pastoris* (EP 183,070; Sreekrishna et al., J. Basic Microbiol., 28: 265-278 [1988]); *Candida; Trichoderma reesia* (EP 244,234); *Neurospora crassa* (Case et al., Proc. Natl. Acad. Sci. USA, 76: 5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112: 284-289 [1983]; Tilburn et al., Gene, 26: 205-221 [1983]; Yelton et al., Proc. Natl. Acad. Sci. USA, 81: 1470-1474 [1984]) and *A. niger* (Kelly and Hynes, EMBO J., 4: 475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982).

Suitable host cells for the expression of nucleic acid encoding flagellin-derived peptide of interest are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen. Virol., 36: 59 (1977)); Chinese hamster ovary cells/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

General Methods for Purification of the Flagellin-Derived Peptide of Interest

Forms of flagellin-derived peptide of interest may be recovered from culture medium or from host cell lysates.

If membrane-bound, it can be released from the membrane using a suitable detergent solution (e.g., TRITON-X™ 100) or by enzymatic cleavage.

Cells employed in expression of nucleic acid encoding the flagellin-derived peptide of interest can be disrupted by various physical or chemical means, such as freeze-thaw cycling, sonication, mechanical disruption, or cell-lysing agents.

It may be desired to purify the polypeptide of interest from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; Protein A Sepharose columns to remove contaminants such as IgG; and metal chelating columns to bind epitope-tagged forms of the flagellin-derived peptide of interest.

Various methods of protein purification may be employed and such methods are known in the art and described, for example, in Deutscher, Methods in Enzymology, 182 (1990); Scopes, Protein Purification: Principles and Practice (Springer-Verlag: New York, 1982). The purification step(s) selected will depend, for example, on the nature of the production process used and the particular flagellin-derived peptide produced.

In a preferred embodiment, the flagellin-derived peptide is purified from the supernatant of recombinant S. Typhimurium SIN41 (fliC fljB), as disclosed in the Examples.

In particular, Salmonella were grown in Luria-Bertani (LB) broth for 6-18 hours at 37° C. with agitation. The supernatant was filtered and saturated with 60% ammonium sulfate (Sigma Aldrich, USA). The precipitated materials were recovered by centrifugation, solubilization in 20 mM Tris/HCl pH7.5 and then dialysis. The proteins were further purified by successive rounds of hydroxyapatite, anion exchange, and size exlusion chromatography (Bio-Rad Laboratories, USA; GE Healthcare, Sweden). Lastly, the proteins were depleted of lipopolysaccharide (LPS) using a polymyxin B column (Pierce, USA). Using the *Limulus* assay (Associates of Cape Cod Inc., USA), the residual LPS concentration was determined to be less than 30 µg LPS per µg recombinant flagellin.

Purification of the Flagellin-Derived Peptide of Interest by Immunoaffinity Chromatography In further embodiments, a flagellin-derived peptide according to the invention may be purified by separation on an immunoaffinity chromatography substrate.

The said immunoaffinity chromatography substrate comprise anti-flagellin antibodies that have been immobilized thereon. By "anti-flagellin" antibodies, it is intended herein antibodies that bind to either a native flagellin or to a hypervariable region-deleted flagellin, including those encompassed by the present invention.

Preferably, the anti-flagellin antibodies consist of monoclonal antibodies, including mouse anti-flagellin antibodies.

It has been shown according to the invention that anti-flagellin antibodies that have been obtained by a method comprising a step of immunizing mice with the hypervariable region-deleted flagellin $FliC_{\Delta 174-400}$ that is disclosed elsewhere in this specification, recognize both native flagellin and any one of the hypervariable region-deleted flagellins that are disclosed herein.

Thus, in certain preferred embodiments of an immunoaffinity chromatography substrate, the said substrate comprise mouse monoclonal antibodies directed against $FliC_{\Delta 174-400}$.

The said preferred immunoaffinity chromatography substrate may be prepared as follows:

Mouse ascite containing anti-$FliC_{\Delta 174-400}$ monoclonal antibodies were purified on Econo-Pac protein A columns (#732-2022 Affi-gel; Bio-Rad).

The resulting purified anti-$FliC_{\Delta 174-400}$ monoclonal antibodies (that may be also termed "B23C5") were covalently coupled via primary amino groups to N-hydroxysuccinimide-activated Sepharose™ high performance column (#17-0716-01 Hitrap NHS activated HP from GE Healthcare), giving rise to the flagellin-specific affinity column. The coupling yield was 98%.

As shown in the examples herein, the above flagellin-specific affinity column allows a highly specific separation of native flagellin, and thus also of any one of the hypervariable region-deleted flagellins that are disclosed herein, from the other protein constituents or non-protein constituents contained in the starting sample.

A method for purifying flagellin or any one of the hypervariable region-deleted flagellins that are disclosed herein is described below:

Flagellin-containing supernatants from culture of recombinant *S. Typhimurium* SIN41 or *E. coli* were centrifugated, filtered through a 0.22 µm membrane, diluted one to one with binding buffer (75 mM Tris-HCl pH8) and applied onto the flagellin-specific affinity column described above.

Then, the flagellin-specific affinity column was washed with 15-20 CV (column volume) of binding buffer.

Then, proteins were eluted with 3 CV of elution buffer (100 mM glycine-HCl, 0.5M NaCl, pH2.7) and fractions were immediately neutralized with 500 µL Tris 1.5M pH8.9 to avoid prolonged exposure to acidic pH.

Then, the column was regenerated with 10 CV of binding buffer and stored at 4° C. with 0.02% sodium azide.

A typical chromatography profile is illustrated in FIG. 13, which depicts both (i) the absorbance (O.D.) curve at 280 nm (line with filled squared boxes) and (ii) the electro conductivity curve. The arrowed numbers in FIG. 13 correspond to the time periods where fractions of the liquid flowing out from the column have been successively collected in view of further analysis of their flagellin content (See FIG. 14 and the paragraph below). The numbered collected fractions consist of, respectively:

no 1-5 µL of the sample before applying (3 µg)=input total quantity=900 µg no 2-20 µL from the sample applied after column run no 3-20 µL from column wash no 4-20 µL from column wash no 5, 6 & 7-20 µL from each of the respective fractions after elution buffer: total quantity≈900 µg no 8-20 µL from column re-equilibration FIG. 14 depicts the photograph of a Western blot assay that has been performed using fractions 1 to 8 referred to in FIG. 13 as the respective starting material.

2. Chemical Synthesis

In certain embodiments, a peptide of the invention may be synthesised through conventional techniques of chemical peptide synthesis.

For instance, the flagellin-derived peptide sequence of interest may be produced by direct peptide synthesis using solid-phase techniques, like those described by Stewart et al., Solid-Phase Peptide Synthesis (W.H. Freeman Co.: San Francisco, Calif., (1969); Merrifield, J. Am. Chem. Soc., 85: 2149-2154 (1963); Fields G B, Noble R L; 1990; Int. J. Pept. Protein Res.; Vol. 35: 161-214).

In vitro protein synthesis may be performed using manual techniques or by automation. Automated synthesis may be accomplished, for instance, with an Applied Biosystems Peptide Synthesizer (Foster City, Calif.) using manufacturer's instructions.

Various portions of the peptide of interest may be chemically synthesized separately and combined using chemical or enzymatic methods to produce the full-length peptide of interest.

Compositions Comprising a Flagellin-Derived Peptide of the Invention

A further object of the invention consists of a composition, in particular a pharmaceutical composition, comprising an adjuvant compound as defined in the present description, in combination notably with one or more pharmaceutically acceptable excipients.

The present invention also pertains to an immunogenic composition comprising an immunoadjuvant compound as defined in the present specification, together with one or more antigens.

An "immunogenic composition", once it has been administered to a subject or an animal, elicits a protective immune response against the said one or more antigen(s) which is (are) comprised herein.

The present invention also concerns a vaccine composition comprising an immunoadjuvant compound as defined in the present specification, together with one or more antigens.

As used herein, a vaccine composition, once it has been administered to the subject or the animal, induces a protective immune response against, for example, a microorganism, or to efficaciously protect the subject or the animal against infection.

A vaccine composition is useful for preventing or ameliorating a pathological condition that will respond favorably to immune response modulation.

Immunoadjuvant

As above-mentioned, the term "immunoadjuvant" when used in reference to an immunogenic composition or vaccine, is intended to mean a substance that acts generally to accelerate, prolong, or enhance the quality of specific immune responses to an antigen.

The immunoadjuvant can advantageously also reduce the number of immunizations or the amount of antigen required for protective immunization.

Antigen

A variety of substances can be used as antigens in a compound or formulation, of immunogenic or vaccine type. For example, attenuated and inactivated viral and bacterial pathogens, purified macromolecules, polysaccharides, toxoids, recombinant antigens, organisms containing a foreign gene from a pathogen, synthetic peptides, polynucleic acids, antibodies and tumor cells can be used to prepare (i) an immunogenic composition useful to induce an immune response in a individual or (ii) a vaccine useful for treating a pathological condition.

Therefore, a flagellin-derived peptide of the invention can be combined with a wide variety of antigens to produce an immunogenic composition or a vaccine useful for inducing an immune response in an individual.

Those skilled in the art will be able to select an antigen appropriate for treating a particular pathological condition and will know how to determine whether a crude or isolated antigen is favored in a particular vaccine formulation.

Those skilled in the art will be also able to determine whether it is preferable to covalently link, or not covalently link, the immunoadjuvant of the invention to the said one or more antigens.

The present in vivo tests demonstrated that mucosal adjuvant activity does not need any link between the flagellin-derived peptide of interest and the target antigen, when administered together via mucosal route, and in particular intranasal route.

An isolated antigen can be prepared using a variety of methods well known in the art. A gene encoding any immunogenic polypeptide can be isolated and cloned, for example, in bacterial, yeast, insect, reptile or mammalian cells using recombinant methods well known in the art and described, for example in Sambrook et al., Molecular Cloning: A Laboratory Manual, Cold Spring Harbor Laboratory, New York (1992) and in Ansubel et al., Current Protocols in Molecular Biology, John Wiley and Sons, Baltimore, Md. (1998). A number of genes encoding surface antigens from viral, bacterial and protozoan pathogens have been successfully cloned, expressed and used as antigens for vaccine development. For example, the major surface antigen of hepatitis B virus, HbsAg, the P subunit of choleratoxin, the enterotoxin of *E. coli*, the circumsporozoite protein of the malaria parasite, and a glycoprotein membrane antigen from Epstein-Barr virus, as well as tumor cell antigens, have been expressed in various well known vector/host systems, purified and used in vaccines.

A flagellin-derived peptide of the invention induces an innate immune response through TLR5-mediated mucosal system that can beneficially enhance an immune response to a recombinant antigen.

A pathologically aberrant cell to be used in a vaccine can be obtained from any source such as one or more individuals having a pathological condition or ex vivo or in vitro cultured cells obtained from one or more such individuals, including a specific individual to be treated with the resulting vaccine.

Immunomodulatory Molecules

A variety of immunomodulatory molecules can also be used in combination with the flagellin-derived peptide of the invention, to alter an immune response in an individual. The type of alteration desired will determine the type of immunomodulatory molecule selected to be combined with the said flagellin-derived peptide of the invention.

For example, to enhance the innate immune response, the flagellin-derived peptide of the invention can be combined with another immunomodulatory molecule that promotes an innate immune response, such as other PAMP or conserved region known or suspected of inducing an innate immune response. A variety of PAMPs are known to stimulate the activities of different members of the toll-like family of receptors.

Such PAMPs can be combined to stimulate a particular combination of toll-like receptors that induce a beneficial cytokine profile. For example, PAMPs can be combined to stimulate a cytokine profile that induces a Th1 or Th2 immune response.

Other types of immunomodulatory molecules that promote humoral or cell-mediated immune responses can be combined with a flagellin-derived peptide of the invention. For example, cytokines can be administered to alter the balance of Th1 and Th2 immune responses. Those skilled in the art will know how to determine the appropriate cytokines useful for obtaining a beneficial alteration in immune response for a particular pathological condition.

Administration of the Flagellin-Derived Peptide of the Invention

The flagellin-derived peptide of the invention will be administered in "immunogenic amount" with one or more molecules, which intended to mean an amount, such as an antigen or other immunomodulatory molecule, required to trigger an immune response.

The dosage of flagellin-derived peptide of the invention, independently or in combination with one or more molecules, will depend, for example, on the pathological condition to be treated, the weight and condition of the individual and previous or concurrent therapies. The appropriate amount considered to be an immunogenic dose for a particular application of the method can be determined by those skilled in the art. Those skilled in the art will understand that the condition of the patient needs to be monitored through the course of therapy and that the amount of the composition that is administered can be adjusted according to patient response to therapy.

As an vaccine immunoadjuvant, the flagellin-derived peptides of the invention can contribute to the effectiveness of the vaccine by, for example, enhancing the immunogenicity of weaker antigens such as highly purified or recombinant antigens, reducing the amount of antigen required for an immune response, reducing the frequency of immunization required to provide protective immunity, improve the efficacy of vaccines in individuals with reduced or weakened immune responses, such as newborns, the aged, and immunocompromised individuals, and enhance the immunity at a target tissue, such as mucosal immunity, or promote cell-mediated or humoral immunity by eliciting a particular cytokine profile.

The flagellin-derived peptide of the invention induces an innate immune response through activation of TLR5 system, in particular here TLR5-mediated mucosal response when administered by mucosal route.

In particular, in vivo tests show that the flagellin-derived peptide of the invention exhibit mucosal adjuvant activity, which able to potentate systemic and mucosal responses against an target antigen.

The innate immune response increases the immune response to an antigen by stimulating the adaptive immune response. Therefore, a combination of the flagellin-derived peptide of the invention, with one or more antigens provides an effective immunogenic composition or vaccine for inducing an immune response in an individual.

A combination of an antigen and/or immunomodulatory molecule, with a flagellin-derived peptide of the invention, can be tested in a variety of preclinical toxicological and safety studies well known in the art.

For example, such a combination can be evaluated in an animal model in which the antigen has been found to be immunogenic and that can be reproducibly immunized by the same route proposed for human clinical testing.

A combination of an antigen and/or immunomodulatory molecule, with a flagellin-derived peptide of the invention, can be tested, for example, by an approach set forth by the Center for Biologics Evaluation and Research/Food and Drug Administration and National Institute of Allergy and Infectious Diseases (Goldenthal, K L et al. AID Res Hum Retroviruses, 9: S45-9 (1993)).

Those skilled in the art will know how to determine for a particular combination of antigen and/or immunomodulatory molecule, with flagellin-derived peptide of the invention, the appropriate antigen payload, route of immunization, volume of dose, purity of antigen, and vaccination regimen useful to treat a particular pathological condition in a particular animal species.

An immunogenic composition or a vaccine of the invention, for inducing an immune response, can be administered as a solution or suspension together with a pharmaceutically acceptable medium.

Such a pharmaceutically acceptable medium can be, for example, water, phosphate buffered saline, normal saline or other physiologically buffered saline, or other solvent or vehicle such as glycol, glycerol, and oil such as olive oil or an injectable organic ester. A pharmaceutically acceptable medium can also contain liposomes or micelles, and can contain immunostimulating complexes prepared by mixing polypeptide or peptide antigens with detergent and a glycoside, such as Quil A.

Further methods for preparing and administering a flagellin-derived peptide of the invention in a pharmaceutically acceptable medium are presented below, in reference to compounds that induce a TLR5-mediated mucosal response.

The immunogenic composition or vaccine of the invention can be administered by a variety of routes to stimulate an immune response. For example, these immunomodulatory molecules can be delivered subcutaneously, intradermally, intralymphatically, intramuscularly, intratumorally, intravesically, intraperitoneally and intracerebrally.

Those skilled in the art will know how to select appropriate delivery routes for particular formulations of flagellin-derived peptides of the invention.

In a preferred embodiment of the invention, vaccination methods for treating or preventing infection in a mammal comprises use of the vaccine of the invention to be administered by particularly a mucosal (e.g., ocular, intranasal, oral, gastric, pulmonary, intestinal, rectal, vaginal, or urinary tract) surface.

Nasal delivery routes may be useful for inducing both mucosal and systemic immune responses. A variety of devices are possible for convenient and effective delivery of formulations to the nasal cavity and pulmonary tissues.

The nasal delivery route may be particularly interesting here since the flagellin-derived peptide of the invention shows a significant adjuvant activity in the mucosa compartment, without having any significant systemic pro-inflammatory side effect.

In a vaccination protocol, the vaccine may be advantageously administered by the mucosal route, as a unique dose or preferably, several times e.g., twice, three or four times at week or month intervals, according to a prime/boost mode. The appropriate dosage depends upon various parameters.

The vaccination protocol may be a strict mucosal protocol or a mix protocol in which the priming dose of the vaccine is administered by the mucosal e.g., intranasal route and the boosting dose(s) is (are) parenterally administered or vice versa.

Formulation

Methods of preparing pharmaceutical formulations or compositions include the step of bringing the active ingredient(s) into association with the carrier and, optionally, one or more accessory ingredients.

In general, the formulations are prepared by uniformly and intimately bringing the active ingredient(s) into association with liquid carriers, or finely divided solid carriers, or both, and then, if necessary, shaping the product.

Liquid dosage forms for oral administration of the active ingredients include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient(s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredient(s) with one or more suitable non-irritating excipients or carriers comprising, for example, cocoa butter, polyethylene glycol, a suppository wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate Pharmaceutical compositions of this invention suitable for parenteral administration comprise the active ingredient(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly (orthoesters) and poly(anhydrides). Depot injectable formulations are also prepared by entrapping the active ingredient(s) in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The amount of antigen, and immunoadjuvant compound in the vaccine composition according to the invention, the dosages administered, are determined by techniques well known to those skilled in the pharmaceutical art, taking into consideration such factors as the particular antigen, the age, sex, weight, species, and condition of the particular animal or patient, and the route of administration.

In a preferred embodiment, the vaccine composition according to the invention, further comprises one or more components selected from the group consisting of surfactants, absorption promoters, water absorbing polymers, substances which inhibit enzymatic degradation, alcohols, organic solvents, oils, pH controlling agents, preservatives, osmotic pressure controlling agents, propellants, water and mixture thereof.

The vaccine composition according to the invention can further comprise a pharmaceutically acceptable carrier. The amount of the carrier will depend upon the amounts selected for the other ingredients, the desired concentration of the antigen, the selection of the administration route, oral or parenteral, etc. The carrier can be added to the vaccine at any convenient time. In the case of a lyophilised vaccine, the carrier can, for example, be added immediately prior to administration. Alternatively, the final product can be manufactured with the carrier.

Examples of appropriate carriers include, but are not limited to, sterile water, saline, buffers, phosphate-buffered saline, buffered sodium chloride, vegetable oils, Minimum Essential Medium (MEM), MEM with HEPES buffer, etc.

Optionally, the vaccine composition of the invention may contain conventional, secondary adjuvants in varying amounts depending on the adjuvant and the desired result. The customary amount ranges from about 0.02% to about 20% by weight, depending upon the other ingredients and desired effect.

Examples of suitable secondary adjuvants include, but are not limited to, stabilizers; emulsifiers; aluminum hydroxide; aluminum phosphate; pH adjusters such as sodium hydroxide, hydrochloric acid, etc.; surfactants such as Tween® 80 (polysorbate 80, commercially available from Sigma Chemical Co., St. Louis, Mo.); liposomes; iscom adjuvant; synthetic glycopeptides such as muramyl dipeptides; extenders such as dextran or dextran combinations, for example, with aluminum phosphate; carboxypolymethylene; bacterial cell walls such as mycobacterial cell wall extract; their derivatives such as *Corynebacterium parvum; Propionibacterium* acne; *Mycobacterium bovis*, for example, Bovine Calmette Guerin (BCG); vaccinia or animal poxvirus proteins; subviral particle adjuvants such as orbivirus; cholera toxin; N,N-dioctadecyl-N',N'-bis(2-hydroxyethyl)-propanediamine (pyridine); monophosphoryl lipid A; dimethyldioctadecylammonium bromide (DDA, commercially available from Kodak, Rochester, N.Y.); synthetics and mixtures thereof. Desirably, aluminum hydroxide is admixed with other secondary adjuvants or an immunoadjuvant such as Quil A.

Examples of suitable stabilizers include, but are not limited to, sucrose, gelatin, peptone, digested protein extracts such as NZ-Amine or NZ-Amine AS. Examples of emulsifiers include, but are not limited to, mineral oil, vegetable oil, peanut oil and other standard, metabolizable, nontoxic oils useful for injectables or intranasal vaccines compositions.

For the purpose of this invention, these adjuvants are identified herein as "secondary" merely to contrast with the above-described immunoadjuvant compound, consisting of a Rho GTPase activator, that is an essential ingredient in the vaccine composition for its effect in combination with an antigenic substance to significantly increase the humoral immune response to the antigenic substance. The secondary adjuvants are primarily included in the vaccine formulation as processing aids although certain adjuvants do possess immunologically enhancing properties to some extent and have a dual purpose.

Conventional preservatives can be added to the vaccine composition in effective amounts ranging from about 0.0001% to about 0.1% by weight. Depending on the preservative employed in the formulation, amounts below or above this range may be useful. Typical preservatives include, for example, potassium sorbate, sodium metabisulfite, phenol, methyl paraben, propyl paraben, thimerosal, etc.

The choice of inactivated, modified or other type of vaccine composition and method of preparation of the improved vaccine composition formulation of the present invention are known or readily determined by those of ordinary skill in the art.

A pharmacologically effective amount of the immunoadjuvant compound according to the invention may be given, for example orally, parenterally or otherwise, and in preference via mucosal route, concurrently with, sequentially to or shortly after the administration of a an antigenic substance in order to potentiate, accelerate or extend the immunogenicity of the antigen.

While the dosage of the vaccine composition depends notably upon the antigen, species of the host vaccinated or to be vaccinated, etc., the dosage of a pharmacologically effective amount of the vaccine composition will usually range from about 0.01 µg to about 500 µg (and in particular 50 µg to about 500 µg) of the immunoadjuvant compound of the invention per dose (base notably on the results shown FIG. 6).

Although the amount of the particular antigenic substance in the combination will influence the amount of the immunoadjuvant compound according to the invention, necessary to improve the immune response, it is contemplated that the practitioner can easily adjust the effective dosage amount of the immunoadjuvant compound through routine tests to meet the particular circumstances.

As a general rule, the vaccine composition of the present invention is conveniently administered orally, parenterally (subcutaneously, intramuscularly, intravenously, intradermally or intraperitoneally), intrabuccally, intranasally, or transdermally. The route of administration contemplated by the present invention will depend upon the antigenic substance and the co-formulants. For instance, if the vaccine composition contains saponins, while non-toxic orally or intranasally, care must be taken not to inject the sapogenin glycosides into the blood stream as they function as strong hemolytics. Also, many antigens will not be effective if taken orally. Preferably, the vaccine composition is administered subcutaneously, intramuscularly or intranasally.

The dosage of the vaccine composition will be dependent notably upon the selected antigen, the route of administration, species and other standard factors. It is contemplated that a person of ordinary skill in the art can easily and readily titrate the appropriate dosage for an immunogenic response for each antigen to achieve the effective immunizing amount and method of administration.

As already specified elsewhere in the present description, a further object of the invention is a vaccine composition according to the invention, for administration to a mucosal surface.

This mode of administration presents a great interest. Indeed, the mucosal membranes contain numerous of dendritic cells and Langerhans cells, which are excellent antigen detecting and antigen presenting cells. The mucosal membranes are also connected to lymphoid organs called mucosal associated lymphoid tissue, which are able to forward an immune response to other mucosal areas. An example of such an epithelia is the nasal epithelial membrane, which consists of practically a single layer of epithelial cells (pseudostratified epithelium) and the mucosal membrane in the upper respiratory tract is connected to the two lymphoid tissues, the adenoids and the tonsils. The extensive network of blood capillaries under the nasal mucosal of the high density of B and T cells, are particularly suited to provide a rapid recognition of the antigen and provide a quick immunological response.

Preferably, the mucosal surface is selected from the group consisting of mucosal surfaces of the nose, lungs, mouth, eye, ear, gastrointestinal tract, genital tract, vagina, rectum, and the skin.

EXAMPLES

Example 1

Immunoadjuvant Effect of Hypervariable Region-Deleted Flagellins

Materials and Methods
Production of Recombinant Flagellins.

The recombinant flagellins originated from the *Salmonella enterica* Serovar *Typhimurium* ATCC14028 flagellin FliC (accession number AAL20871).

The flagellins FliC and FliC$_{\Delta 205-293}$ were either isolated from the *S. Typhimurium* strains SIN22 (fljB) and SJW46, as described previously (Yoshioka et al, 1995. Flagellar filament structure and cell motility of *Salmonella typhimurium* mutants lacking part of the outer domain of flagellin. J. Bacteriol. 177:1090-1093; Didierlaurent et al, 2004. Flagellin Promotes Myeloid Differentiation Factor 88-Dependent Development of Th2-Type Response. J. Immunol. 172: 6922-6930; Sierro et al, 2001, Flagellin stimulation of intestinal epithelial cells triggers CCL20-mediated migration of dendritic cells. Proc. Natl. Acad. Sci. USA 98:13722-13727) or purchased from Alexis Biochemicals (Switzerland).

The constructs encoding $FliC_{\Delta 174-400}$ and $FliC_{\Delta 191-352}$ were generated by PCR on a pBR322-derived plasmid harboring the wild type fliC gene SEQ ID No 3, under the control of its own promoter and using the following primer pairs: AGCACCattcagcgtatccagacc (SEQ ID No 15)/GCTGGTgctacaaccaccgaaaac (SEQ ID No 16), and TCGAGatctctgtaacagttgcagcc (SEQ ID No 17)/ACTCGAGgacggtacatccaaaactgcac (SEQ ID No 18) (bases encoding a linker are in italics).

Site-directed mutagenesis was also performed on the plasmid harboring $FliC_{\Delta 174-400}$ in order to replace the residues 89-96 (QRVRELAV) SEQ ID No. 34 involved in TLR5 detection by the corresponding sequences from a non-signaling flagellin (DTVKVKAT) SEQ ID No. 35; the resulting protein was thus $FliC_{\Delta 174-400/89-96}*$. In $FliC_{\Delta 174-400}$, $FliC_{\Delta 191-352}$ and $FliC_{\Delta 174-400/89-96}*$, the asparagine located 6 residues from the end was changed into a serine.

In $FliC_{\Delta 174-400}$, $FliC_{\Delta 191-352}$ and $FliC_{\Delta 174-400/89-96}*$, the asparagine located 6 residues from the end was changed into a serine.

The truncated flagellins were purified from the supernatant of recombinant *S. Typhimurium* SIN41 (fliC fljB), as follows. *Salmonella* were grown in Luria-Bertani (LB) broth for 18 hours at 37° C. with agitation. The supernatant was filtered and saturated with 60% ammonium sulfate (Sigma Aldrich, USA). The precipitated materials were recovered by centrifugation, solubilization in 20 mM Tris/HCl pH7.5 and then dialysis. The proteins were further purified by successive rounds of hydroxyapatite and anion exchange chromatography (Bio-Rad Laboratories, USA). Lastly, the proteins were depleted of lipopolysaccharide (LPS) using a polymyxin B column (Pierce, USA). Using the *Limulus* assay (Associates of Cape Cod Inc., USA), the residual LPS concentration was determined to be less than 30 μg LPS per μg recombinant flagellin.

When specified, flagellins were treated for 1 h at 37° C. with 0.017% trypsin-EDTA (Invitrogen, USA) to totally hydrolyze the proteins, followed by heating at 70° C. for 1 h to inactivate the trypsin. Proteins were analyzed using standard SDS-PAGE and immunoblotting with FliC-specific polyclonal antibodies.

Animal Experiments.

Female NMRI mice (6-8 weeks old) were purchased from Charles River Laboratories (France) and maintained in a specific pathogen-free facility in an accredited establishment (#A59107; Institut Pasteur de Lille). All experiments complied with current national and institutional regulations and ethical guidelines.

For hyper-immunization, animals were injected subcutaneously (s.c.) with the flagellin FliC (1 μg per injection) emulsified in 200 μl of complete Freund's adjuvant (CFA)/PBS on day 1 and incomplete Freund's adjuvant (IFA)/PBS on days 21, 35 and 49. On day 63, mice were given 200 μl flagellin/PBS i.v. and were sacrificed 2 h later by intraperitoneal (i.p.) injection of 5 mg sodium pentobarbital (CEVA Santé Animale, France) for serum and tissue sampling and analysis.

To characterize the mucosal innate response and adjuvant properties, 20 μl of PBS±proteins were administered intranasally (i.n.) to mice anesthetized i.p. with 1.5 mg ketamine (Merial, France) and 0.3 mg xylazine (Bayer, Germany) per 25 g animal.

To study pro-inflammatory responses, mice were sampled either at 2 h (for RNA and gene expression assays) or 6 h (to test cytokine production).

For immunization assays, mice were administered i.n. with PBS±LPS-depleted ovalbumin (OVA) (20 μg, Sigma, grade VII, USA)±flagellins (1 μg) on days 1 and 21. Broncho-alveolar lavages (BALs) and serum were sampled on day 35.

To assess neutralization, immune and mock sera were heated for 30 min at 56° C. to inactivate complement. Serial serum dilutions (in 200 μl of PBS) were passively transferred to animals by the i.v. route 1 h before systemic activation with flagellins. In some experiments, sera were mixed with flagellins diluted in PBS and administered i.n. to test mucosal neutralization.

BALs were collected after the intra-tracheal injection of 1 ml PBS with Complete Protease Inhibitor Cocktail (Roche, Switzerland) and clarified by centrifugation.

Blood samples were collected and clotted at room temperature, with the serum then being separated by centrifugation.

Lung protein extracts were prepared by homogenizing tissue with 2 ml T-PER Tissue Protein Extraction Reagent (Pierce, USA) supplemented with protease inhibitors. All samples were stored at −80° C. prior to analysis.

Analysis of Antigen-Specific Antibody Responses.

Levels of OVA- or flagellin-specific antibodies in serum and BAL samples were assessed using ELISAs.

Briefly, OVA (20 μg per well in phosphate buffer 0.2M pH 6.5) and flagellin FliC (100 ng per well in PBS) were coated on MaxiSorp microplates (Nalge Nunc Int., USA) overnight at 4° C. All microplates were washed with PBS/Tween20 0.05% and then blocked with PBS/Dry Milk 1% for 1 h at room temperature.

Serial dilutions of samples were incubated for 1 h at room temperature before development. Biotinylated anti-mouse IgG or IgA antibodies (Southern Biotechnology Associates, USA), HRP-conjugated streptavidin (GE Healthcare, USA) and 3,3',5,5' tetramethylbenzidine (Becton Dickinson Bioscience, USA) were used as development reagents. The reaction was stopped by addition of $H_2SO_4$ and the OD at 450 nm was determined.

The IgG titer was defined as the reciprocal of the highest sample dilution yielding an absorbance value of 0.15 OD for OVA and 0.5 OD for FliC and was systematically compared with a reference serum. Titers are given as geometrical means of titers from individual mice.

Total IgA and OVA-specific IgA levels in BALs were measured and normalized using a calibration curve with commercial mouse IgA (Sigma). The specific IgA ratio (expressed in ng of OVA-specific IgA per μg total IgA) was determined for each mouse.

Cytokine-Specific ELISA and Gene Expression.

Mouse CXCL2 and CCL20 and human IL-8 (CXCL8) levels were measured in serum, BALs, total lung and/or cell culture supernatant using commercial ELISA kits (R&D Systems, USA).

Total RNA from mouse lungs was extracted with the Nucleospin RNA II kit (Macherey Nagel, Germany) and reverse-transcribed with the High-Capacity cDNA Archive Kit (Applied Biosystems, USA). The resulting cDNA was amplified using SYBR Green-based real-time PCR (Applied Biosystems).

The specific primers are CGTCATCCATGGCGAACTG (SEQ ID No 19)/GCTTCTTTGCAGCTCCTTCGT (SEQ ID No 20) (ACTB, coding for β-actin), TTTTGGGATGGAATTGGACAC (SEQ ID No 21)/TGCAGGTGAAGC- CTTCAACC (SEQ ID No 22) (CCL20), and CCCT-CAACGGAAGAACCAAA (SEQ ID No 23)/CACATCAGGTACGATCCAGGC (SEQ ID No 24) (CXCL2). Relative mRNA levels ($2^{-\Delta\Delta ct}$) were determined by comparing (a) the PCR cycle thresholds (Ct) for the gene of interest and ACTB ($\Delta$Ct) and (b) $\Delta$Ct values for treated and control groups (A$\Delta$Ct), as described previously (Sierro et al, 2001, Flagellin stimulation of intestinal epithelial cells triggers CCL20-mediated migration of dendritic cells. Proc. Natl. Acad. Sci. USA 98:13722-13727).

Cell-Based Assays.

The Caco-2 human colon adenocarcinoma cell line was stably transfected with the plasmid harboring a luciferase gene under the control of the human CCL20 promoter (Rumbo et al, 2004, Lymphotoxin beta receptor signaling induces the chemokine CCL20 in intestinal epithelium. Gastroenterol. 127:213-223), giving rise to the Caco-Rumbo line.

These intestinal epithelial cells were grown in Dulbecco's Modified Eagle's Medium supplemented with 10% fetal calf serum, 10 mM HEPES, non-essential amino acids 1×, penicillin (100 U/ml) and streptomycin (100 U/ml) and (for transgene selection) 0.7 mg/mL G418 (Invitrogen).

The human bronchial epithelial cell line BEAS-2B was cultured in Kaigh's F12 nutrient medium supplemented as for Caco-Rumbo medium plus 1 mM sodium pyruvate and insulin-transferrin-selenium mix (Invitrogen).

Cells were stimulated with recombinant flagellins for 6 h for luciferase assays or for 16 h before harvesting the supernatant for ELISA.

Luciferase activity in cell extracts was measured using the Bright Glo Luciferase Assay (Promega, USA). Relative luminescence (RLU) was normalized as a percentage of the maximum activity with wild type flagellin for the activation test with the recombinant flagellins. For the in vitro neutralization test, the RLU was normalized as a percentage of the maximum activity for each protein: [(RLU$_{treated}$/RLU$_{untreated}$)/(RLU$_{max}$/RLU$_{untreated}$)]×100.

Statistical Analysis.

Statistical differences were analyzed using the Mann-Whitney test and were considered to be significant for p values <0.05. Unless otherwise specified, results are expressed as arithmetic means±standard deviation.

Résultats

Figure 1:
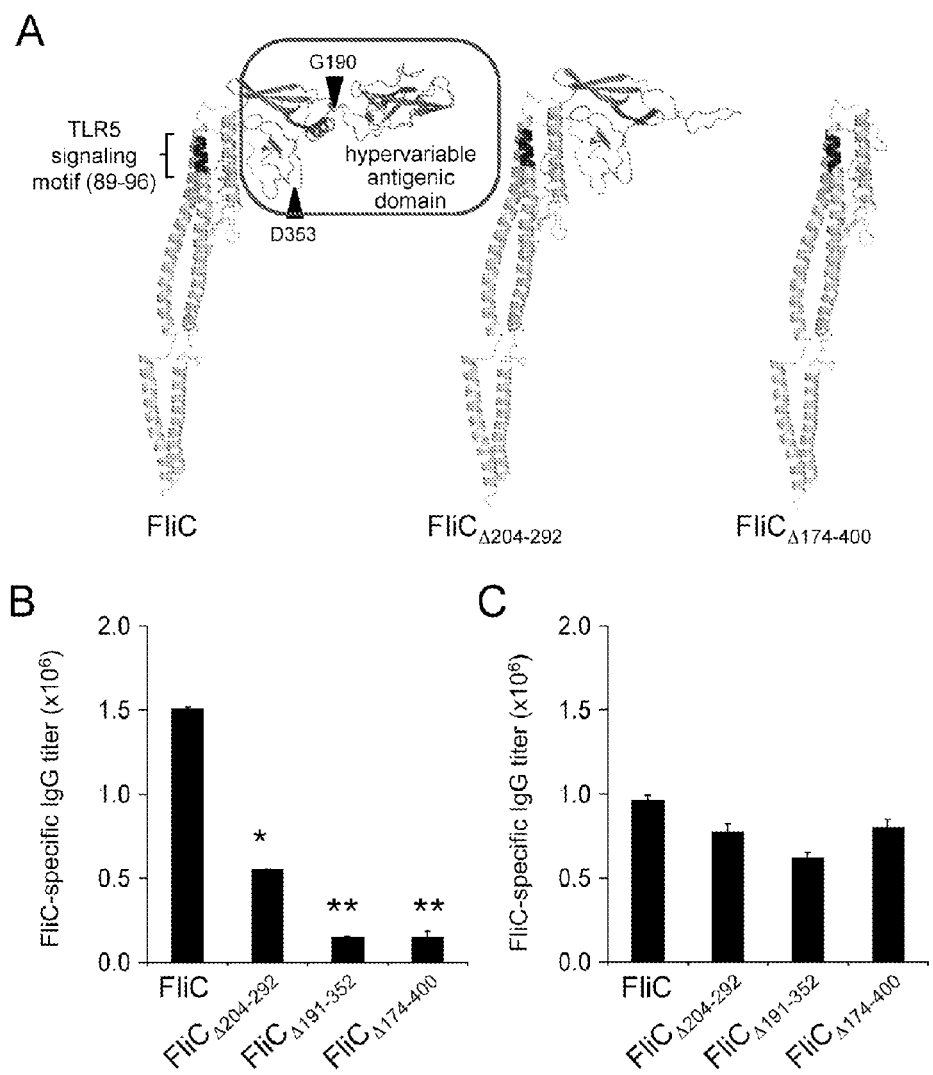
FIG. 1. Characteristics and cross-reactivity of hypervariable region-deleted flagellins.

Deletion of Flagellin's Hypervariable Region Impairs Antigenicity but does not Modify TLR5-Stimulating Activity Two novel flagellin molecules (FliC$_{\Delta 191-352}$ and FliC$_{\Delta 174-400}$, composed respectively of 336 and 271 amino-acids) were constructed by internal deletion (FIG. 1A).

As a control, we used the previously characterized variant FliC$_{\Delta 204-292}$, which has a partial deletion in the antigenic domain (Yoshioka et al, 1995, Flagellar filament structure and cell motility of Salmonella typhimurium mutants lacking part of the outer domain of flagellin. J. Bacteriol. 177:1090-1093) (FIG. 1A).

As a negative control for in vitro and in vivo experiments, mutations that impair TLR5 signaling were introduced into FliC$_{\Delta 174-400}$, yielding the recombinant protein FliC$_{\Delta 174-400/89-96*}$.

The predicted structures of the respective flagellins indicated that the motif 89-96 and the overall structure of the conserved regions were unchanged (FIG. 1A).

With the exception of FliC$_{\Delta 204-292}$, the variants were unable to complement the motility of flagellin-deficient bacteria and were secreted into the culture supernatant.

Next, we assessed the intrinsic antigenicity of the recombinant flagellins. To this end, saturating concentrations of flagellins were coated onto microplates and probed by ELISA, using a hyperimmune serum specific for FliC or FliC$_{\Delta 174-400}$.

As illustrated in FIG. 1B, we observed 3- to 10-fold lower antibody titers when anti-FliC serum was titrated against FliC variants than against wild type FliC.

In contrast, the reactivity of hyperimmune serum specific for FliC$_{\Delta 174-400}$ was similar, whatever the target flagellin (FIG. 10).

These results suggest that the central hypervariable region is the major target for anti-flagellin antibodies.

Lastly, we sought to establish whether or not the recombinant molecules retained any TLR5-stimulating activity.

A dose-response analysis was performed using Caco-Rumbo reporter cells and the lung epithelial cell line BEAS-2B. Activation was assessed by measuring luciferase activity in Caco-Rumbo cells and IL-8 secretion by BEAS-2B cells (human intestinal epithelial cell lines are unique reporters of the flagellin/TLR5-stimulatory activity, based on the expression of chemokines CCL20, also known as "liver-activated and -regulated chemokines" or "LARC, and IL-8).

As shown in FIG. 2A-B, FliC$_{\Delta 204-292}$, FliC$_{\Delta 191-352}$ and FliC$_{\Delta 174-400}$ were all potent cell activators. The flagellins' respective EC50 values varied slightly with the cell type but fell within the previously described ng/mL range (Smith et al, 2003, Toll-like receptor 5 recognizes a conserved site on flagellin protofilament formation and bacterial motility. Nat. Immunol. 4:1247-1253).

The recombinant flagellins' activity was found to be fully dependent on TLR5, since FliC$_{\Delta 174-400/89-96*}$ was unable to activate epithelial cells.

The requirement for TLR5 signaling was further confirmed by using bone marrow macrophages derived from TLR5-deficient mice; the cells did not synthesize any IL-12 p40 upon stimulation with recombinant flagellins (data not shown).

Deleted Flagellins Stimulate TLR5-Dependent Mucosal Innate Responses

TLR5 stimulation by recombinant flagellins was then studied in vivo by the mucosal route.

To this end, CCL20 and CXCL2 expression in the lungs of mice treated i.n. with flagellins was quantified using qRT-PCR (FIG. 2C).

Within 2 hours, CCL20 mRNA pulmonary levels were about 30-fold higher in animals treated with wild type or recombinant flagellins than in mock-treated animals.

Furthermore, CCL20 chemokine production was detected at 6 h post-instillation, both in lung homogenates and BALs (FIG. 2D). In control experiments, FliC$_{\Delta 174-400/89-96*}$ and trypsin-digested flagellins did not induce this type of effect. Similar findings were observed for CXCL2 (data not shown).

These results confirmed that the in vivo pro-inflammatory response was exclusively due to the recombinant flagellins.

Overall, flagellins with deletions in the hypervariable region displayed mucosal pro-inflammatory properties equivalent to those of the wild type FliC counterpart.

Recombinant Flagellins Exhibit Mucosal Adjuvant Activity

In order to characterize the adjuvant properties of our recombinant molecules, antibody responses in serum and secretions were studied after i.n. immunizations.

Ovalbumin (OVA) was used as a model antigen, formulated with or without the various flagellins or with cholera toxin (CT) as a gold standard mucosal adjuvant.

The co-administration of FliC with OVA significantly increased the OVA-specific IgG response (both in serum and the BAL, about 300- and 100-fold, respectively), compared with animals immunized with OVA alone (FIG. 3A-B).

Moreover, the OVA-specific IgA response was enhanced in BAL, thereby suggesting that FliC promotes the archetypal secretory antibody response of a mucosal adjuvant (FIG. 3C). Interestingly, FliC's effect was similar to that of CT.

Like FliC, the recombinant flagellins $FliC_{\Delta 204-292}$, $FliC_{\Delta 191-352}$ and $FliC_{\Delta 174-400}$ were thus able to potentate systemic and mucosal responses.

In contrast, $FliC_{\Delta 174-400/89-96*}$ and trypsin-treated flagellins lacked potency (FIG. 3 and Table 1).

Hence, the deletion of flagellin's hypervariable region did not significantly influence the TLR5-mediated mucosal adjuvant properties. Our data also showed that the recombinant molecules' respective effects on innate and adaptive immunity are correlated.

Deletion of the Hypervariable Region Impairs the Ability to Elicit Anti-Flagellin Antibodies.

Deletion of the antigenic domain is expected to decrease the flagellin-specific immune response and thereby any neutralization of TLR5-mediated immunity, especially with repeated administration.

We therefore decided to assess the efficacy of i.n. immunization with respect to the induction of FliC-specific antibodies.

As shown, FliC elicited a strong IgG response in serum and BALs (Table 1 and FIG. 4). In contrast, $FliC_{\Delta 204-292}$ triggered 10-fold lower antibody levels in both fluids than did FliC and a more pronounced effect was observed after immunization with $FliC_{\Delta 191-352}$ and $FliC_{\Delta 174-400}$.

In conclusion, the flagellins' antigenic and immunostimulatory domains are functionally uncoupled. Therefore, $FliC_{\Delta 191-352}$ and $FliC_{\Delta 174-400}$ are molecules of interest for preventing or attenuating the generation of flagellin-specific antibodies with neutralizing activity.

Flagellin-Specific Antibodies Neutralize TLR5-Mediated Signaling

Bacterial flagellins are known to elicit strong antibody responses, which are mainly directed against the hypervariable region. We hypothesized that anti-flagellin antibodies would neutralize the flagellins' TLR5-stimulating activity.

Hence, mice were immunized s.c. with the flagellin FliC or a mock preparation (PBS alone or the irrelevant antigen ovalbumin (OVA) formulated in CFA), followed by boosts with IFA. ELISA analysis revealed that the anti-FliC sera exhibited specific IgG titers >$10^6$, whereas mock sera titers were below the assay's detection threshold ($10^2$).

As above-mentioned, human intestinal epithelial cell lines are useful as unique reporters of flagellin/TLR5-stimulatory activity, based on expression of the chemokine CCL20 (also known as "liver-activated and -regulated chemokine", LARC).

Thus using Caco-Rumbo cells harboring the luciferase gene under the control of the CCL20 promoter, it is here demonstrated that an anti-FliC serum is able to fully neutralize FliC's TLR5 agonist activity (FIG. 5A).

The neutralizing effect of FliC-specific antibodies on TLR5 signaling was then directly assessed in immunized animals. To this end, systemic pro-inflammatory responses in mice (production of CCL20 and CXCL2 chemokines) were studied after i.v. injection of FliC (FIG. 5B-C)

In mock-immunized animals, a FliC challenge triggered a significant increase in serum levels of CCL20 and CXCL2, compared with a PBS challenge.

In contrast, chemokine production in FliC-immunized animals was not enhanced by any of the challenges. Using passive serum transfer in naïve animals, a close correlation was found between the amount of antibody injected and the systemic innate response, as shown in FIG. 5D.

In conclusion, pre-existing immunity to flagellin can neutralize the latter's TLR5-stimulating activity, both in vitro and in vivo.

This is not the case with $FliC_{\Delta 174-400}$, which is strongly impaired in its capacity to promote the production of flagellin-specific antibodies, including neutralizing antibodies, as disclosed before in accordance with FIG. 4.

The effective doses needed to initiate TLR5-mediated innate responses by the i.n. route, was determined. FliC and $FliC_{\Delta 174-400}$ displayed similar dose-response profiles and the 0.1 μg dose was selected for subsequent neutralization assays (FIG. 6).

To this end, animals were hyper-immunized i.n. with FliC to elicit strong, FliC-specific mucosal IgG responses (mean titer ~45,000) and then challenged i.n. with 0.1 μg FliC or $FliC_{\Delta 174-400}$ flagellins. Pro-inflammatory chemokine production in BALs was monitored.

Challenge with FliC or $FliC_{\Delta 174-400}$ led to CCL20 production (4.28±1.98 vs 1.08±0.54 ng/ml and 2.48±1.22 vs 0.93±0.48 ng/ml in mock- and FliC-immunized mice, respectively) as observed in naïve animals.

Mucosal and Systemic TLR5-Dependent Responses Depend to Different Extents on the Hypervariable Flagellin Region We also wanted to study the neutralization by flagellin-specific antibodies of TLR5-dependent responses induced after i.v. injection of the recombinant flagellins.

To analyze the systemic activation of innate immunity, the production in circulating pro-inflammatory chemokines CCL20 and CXCL2 was measured by ELISA in serum (FIG. 7).

Unexpectedly, we observed that $FliC_{\Delta 174-400}$ was about 100-fold impaired in its ability to trigger systemic pro-inflammatory effects, compared with the wild type FliC.

Whereas 10 μg $FliC_{\Delta 174-400}$ stimulated a slight chemokine production, the variant mutated within the TLR5 motif $FliC_{\Delta 174-400/89-96*}$ was devoid of activity (0.85±0.27 vs 0.02±0.00 ng/ml for CCL20).

This contrasted with $FliC_{\Delta 204-292}$ and $FliC_{\Delta 191-352}$, which were both potent activators like FliC.

Hence, certain molecular determinants on the hypervariable region (or dependent on the latter) are required for systemic TLR5 stimulation but not mucosal TLR5 stimulation. Taken as a whole, our results indicate that TLR5 activation within the mucosal and the systemic compartments is controlled by distinct mechanisms.

Example 2

Biological Activity of Hypervariable Region-Deleted Flagellins Selected from the Group Consisting of $FliC_{\Delta 174-400}$, $FliC_{\Delta 161-405}$, and $FliC_{\Delta 138-405}$ Production of Recombinant Hypervariable Region-Deleted Flagellins.

Various hypervariable region-deleted flagellins were recombinantly produced by performing the same method as disclosed in Example 1 above, namely $FliC_{\Delta 174-400}$, $FliC_{\Delta 161-405}$, and $FliC_{\Delta 138-405}$ and $FliC_{\Delta 100-405}$.

FIGS. 8 and 9 depict analyses of the said recombinantly produced proteins.

FIG. 8 shows the result of a SDS PAGE electrophoresis that has been performed on the recombinant proteins collected from the culture supernatant from the corresponding recombinant S. typhimurium SIN41 bacterial cells, after a step of protein precipitation with TCA.

FIG. 9 shows the result of a Western blotting assay using anti-FliC polyclonal antibodies that has been performed on the culture supernatant from the corresponding recombinant S. typhimurium SIN41 bacterial cells, after a step of protein precipitation with TCA.

Biological Activity of the Hypervariable Region-Deleted Flagellins $FliC_{\Delta174-400}$, $FliC_{\Delta161-405}$, and $FliC_{\Delta138-405}$.

The effect of the $FliC_{\Delta174-400}$, $FliC_{\Delta161-405}$, and $FliC_{\Delta138-405}$ on the induction of CCL20 and CXCL2 was assayed, by performing the cytokine-specific ELISA assay that is described in Example 1.

Briefly, C3H/HeJ (TLR4-deficient) were injected intraperitoneally with 10 μg of the various recombinant flagellins deleted from positions 174-400, 161-405, and 138-405.

After 2 h, serum were sampled and processed for cytokine specific ELISA (CCL20 and CXCL2).

The flagellin preparation were derived from supernatant of recombinant Salmonella that was previously precipitated with ammonium sulfate and dialyzed (FIGS. 8 and 9). Since these crude preparation may be contaminated with endotoxin, we used mice deficient for TR4 signaling since LPS may be a main contaminant in these crude preparation. In addition, we used trypsin-treatment to demonstrate that the biological activity is present in the protein fraction of crude preparations.

The results are depicted in FIGS. 10 (induction of CCL20) and 11 (induction of CXCL2).

The results of FIGS. 10 and 11 suggest that the recombinant flagellins $FliC_{\Delta161-405}$ and $FliC_{\Delta138-405}$ are competent for signaling in vivo as described for $FliC_{\Delta174-400}$.

These results suggest that $FliC_{\Delta161-405}$ and $FliC_{\Delta138-405}$ are effective TLR5 agonists and therefore may represent effective adjuvant compounds.

Example 3

Adjuvant Activity of $FliC_{\Delta174-400}$ on immune Responses Against the gp140 Antigen from the HIV1 Virus Immunization protocols and the analysis of the antigen-specific antibody responses are the same as described in Example 1, except for specific features that may be specified below.

Briefly, adjuvant activity of native Flagellin FliC and recombinant $FliC_{\Delta174-400}$ on HIV1 antigen gp140 was performed as follows: NMRI mice (n=8) were immunized on day 1 and on day 21 intranasally with 20 μl PBS containing gp140 (5 μg per mice) without or with FliC or $FliC_{\Delta174-400}$ (1 μg per mice).

Serum and bronchoalveolar lavages (BAL) were sampled on day 35 and the antibody titer was determined by gp140-specific ELISA.

The results are depicted in FIG. 12, where each symbol represent individual mice and the bar represent the geometric mean.

The symbols mean mice administered intranasally with, respectively: (i) Circles: HIV1 gp140 alone; (ii) diamond: HIV1 gp140+$FliC_{\Delta174-400}$; (iii) triangle: gp140+FliC.

Antibody titers from serum samples are represented as filled symbols on the left part of FIG. 12 (closed symbols). Antibody titers from bronchoalveolar lavage samples are represented as open symbols on the right part of FIG. 12.

The results show that various hypervariable region-deleted fagellins as defined in the present specification consist of effective immunoadjuvant compounds.

TABLE 1

Protease-sensitive immune responses induced by recombinant flagellins*

| Intranasal immunisation* | Anti-OVA IgG** | | | | Anti-FliC IgG** | | | |
|---|---|---|---|---|---|---|---|---|
| | serum | | BAL | | serum | | BAL | |
| | mean | SD | mean | SD | mean | SD | mean | SD |
| PBS | ND*** | 0.0 | ND | 0.0 | ND | 0.0 | ND | 0.0 |
| OVA | 2.4 | 0.8 | 1.1 | 0.7 | ND | 0.0 | ND | 0.0 |
| FliC + OVA | 5.7 | 0.1 | 3.9 | 0.5 | 5.9 | 0.6 | 3.0 | 0.7 |
| $FliC_{\Delta204-292}$ + OVA | 5.5 | 0.9 | 3.4 | 0.8 | 3.3 | 0.8 | 1.0 | 0.5 |
| $FliC_{\Delta191-352}$ + OVA | 4.5 | 1.3 | 2.9 | 0.9 | 2.2 | 0.3 | ND | 0.0 |
| $FliC_{\Delta174-400}$ + OVA | 4.9 | 0.9 | 2.7 | 0.9 | 2.0 | 0.1 | 0.1 | 0.2 |
| TRP + OVA | 3.4 | 1.2 | 1.3 | 0.8 | ND | 0.0 | ND | 0.0 |
| FliC/TRP + OVA | 2.8 | 0.5 | 1.1 | 0.6 | ND | 0.0 | 0.3 | 0.3 |
| $FliC_{D204-292}$/TRP + OVA | 3.0 | 1.4 | 0.8 | 1.0 | ND | 0.0 | ND | 0.0 |
| $FliC_{D191-352}$/TRP + OVA | 2.6 | 0.7 | 0.8 | 0.9 | ND | 0.0 | ND | 0.0 |
| $FliC_{D174-400}$/TRP + OVA | 2.6 | 0.4 | 1.1 | 0.9 | ND | 0.0 | ND | 0.0 |

*Mice (n = 8) were immunized in. with PBS, ovalbumin (OVA), OVA + flagellins/flagellin-derived peptides or OVA + trypsin-treated flagellins (TRP) on days 1 and 21. On day 35, OVA- and FliC-specific IgG titers were measured in the serum and BALs. Statistical significance (p > 0.05) was determined in a Mann-Whitney test.
**Values are expressed as Log10 (reciprocal titers) ± standard deviation (SD). In serum and BAL, limit of detection is 2 and 0.3 (1/100 serum dilution and 1/2 BAL dilution), respectively.
***"ND" stands for "Not Detected".

TABLE 2

Sequences

| SEQ ID N° | Type | Description |
|---|---|---|
| 1 | peptide | Flagellin (FliC) |
| 2 | peptide | $FliC_{\Delta174-400}$ |
| 3 | nucleic acid | Flagellin (FliC) |
| 4 | nucleic acid | primer |
| 5 | nucleic acid | primer |
| 6 | nucleic acid | primer |
| 7 | nucleic acid | primer |
| 8 | nucleic acid | primer |
| 9 | nucleic acid | primer |
| 10 | nucleic acid | primer |
| 11 | nucleic acid | primer |
| 12 | nucleic acid | primer |
| 13 | nucleic acid | primer |
| 14 | nucleic acid | $FliC_{\Delta174-400}$ |
| 15 | nucleic acid | primer |
| 16 | nucleic acid | primer |
| 17 | nucleic acid | primer |
| 18 | nucleic acid | primer |
| 19 | nucleic acid | primer |
| 20 | nucleic acid | primer |
| 21 | nucleic acid | primer |
| 22 | nucleic acid | primer |
| 23 | nucleic acid | primer |
| 24 | nucleic acid | primer |
| 25 | peptide | $FliC_{\Delta161-405}$ |
| 26 | peptide | $FliC_{\Delta138-405}$ |
| 27 | peptide | $FliC_{\Delta100-405}$ |
| 28 | nucleic acid | $FliC_{\Delta161-405}$ |
| 29 | nucleic acid | $FliC_{\Delta138-405}$ |
| 30 | nucleic acid | $FliC_{\Delta100-405}$ |

What is claimed is:

1. An immunoadjuvant compound comprising:
   a) a N-terminal peptide having at least 95% amino acid identity with the amino acid sequence starting from the amino acid residue located at position 1 of SEQ ID No 1 and ending at an amino acid residue selected from the group consisting of any one of the amino acid residues located at positions 99 to 173 of SEQ ID No 1; and
   b) a C-terminal peptide, wherein the said C-terminal peptide is selected from the group consisting of the amino acid sequences 401-494 and 406-494 of SEQ ID NO1,
   wherein:
   the said N-terminal peptide is linked to the said C-terminal peptide one to the other, through a spacer chain, the spacer chain consisting of 1 to 20 amino acids linked by peptide bonds, wherein the amino acids are selected from the 20 naturally-occurring amino acids and
   wherein (i) the said N-terminal and C-terminal peptides consist of the amino acid sequences 1-137 and 406-494 of SEQ ID No 1, respectively; or
   (ii) said N-terminal peptide and the said C-terminal peptide are indirectly linked, one to the other, through an intermediate spacer chain consisting of NH$_2$-Gly-Ala-Ala-Gly-COOH peptide sequence (SEQ ID NO 31).

2. The immunoadjuvant compound of claim 1, wherein the asparagine amino acid residue located at position 488 of SEQ ID No 1 is replaced by a serine.

3. The immunoadjuvant compound of claim 1, wherein the compound comprises an additional methionine residue at the N-terminal end.

4. A pharmaceutical composition comprising the immunoadjuvant compound according to claim 1, together with one or more pharmaceutically acceptable excipients.

5. An immunogenic composition comprising the immunoadjuvant compound according to claim 1, together with one or more antigens.

6. The immunogenic composition according to claim 5 wherein the immunoadjuvant compound is not covalently linked to the said one or more antigens.

7. The immunoadjuvant compound of claim 1, wherein the said N-terminal peptide and the said C-terminal peptide are indirectly linked, one to the other, through an intermediate spacer chain comprising NH$_2$-Gly-Ala-Ala-Gly-COOH peptide sequence (SEQ ID NO 31).

* * * * *